United States Patent

Fukaya et al.

[11] Patent Number: 5,805,335
[45] Date of Patent: Sep. 8, 1998

[54] OPERATING MICROSCOPE

[75] Inventors: Takashi Fukaya, Sagamihara; Koji Yasunaga, Hino; Masahiko Kinukawa, Sagamihara; Hiroshi Fujiwara, Hachioji; Yoshia Hoshino, Hachioji; Junichi Nozawa, Hachioji, all of Japan

[73] Assignee: Olympus Optical Co., Ltd., Japan

[21] Appl. No.: 843,190

[22] Filed: Apr. 14, 1997

[30] Foreign Application Priority Data

Apr. 17, 1996 [JP] Japan .................................. 8-095376

[51] Int. Cl.⁶ .............................. G02B 21/00; A47F 5/00
[52] U.S. Cl. ...................... 359/384; 359/368; 248/281.11
[58] Field of Search .................... 359/368, 382, 359/384; 248/123.11, 280.11, 281.11, 585

[56] References Cited

U.S. PATENT DOCUMENTS

| | | | |
|---|---|---|---|
| 3,787,696 | 1/1974 | Dao et al. | 250/311 |
| 4,593,980 | 6/1986 | Schwartz | 359/391 |
| 4,912,388 | 3/1990 | Tanaka et al. | 318/640 |
| 5,205,522 | 4/1993 | Nakamura | 248/123.1 |
| 5,509,300 | 4/1996 | Chamberlin et al. | 73/105 |

FOREIGN PATENT DOCUMENTS

| | | |
|---|---|---|
| 55-36116 | 9/1980 | Japan . |
| 1-180508 | 7/1989 | Japan . |
| 3-21887 | 3/1991 | Japan . |
| 6-48329 | 6/1994 | Japan . |
| 7-328014 | 12/1995 | Japan . |

*Primary Examiner*—Thong Nguyen
*Assistant Examiner*—Mark A. Robinson
*Attorney, Agent, or Firm*—David E. Dougherty

[57] ABSTRACT

An operating microscope includes a base and a support coupled to the base. An arm has a proximal end portion rotatably and/or vertically movably coupled to the support, and a distal end portion. At least the distal end portion is formed of a non-magnetic material. A microscope portion is coupled to the distal end portion of the arm and includes a stereoscopic optical system for forming an image of an observed part. The microscope portion is formed of a non-magnetic material. The operating microscope also includes a power system for operating the microscope portion or a part thereof, and an operation instructing portion for instructing the power system to operate. The power system includes a power generating portion for generating a pressure change or a positional change; a power output portion, formed of a non-magnetic material, for converting the pressure change or the positional change of the power generating portion into a power for operating the microscope portion and a part thereof; and a power transmitting mechanism for transmitting the pressure change and the positional change from the power generating portion to the power output portion. The power transmitting mechanism is formed of a non-magnetic material at least near the power output portion.

28 Claims, 17 Drawing Sheets

OPERATING MICROSCOPE

BACKGROUND OF THE INVENTION

1. Field of the Invention

This invention relates to an operating microscope for use with an apparatus utilizing magnetism, for example, an image diagnosis apparatus which utilizes nuclear magnetic resonance. The operating microscope performs at least one operation manually or via an operation system in response to an output signal from an operation instructing means for instructing the at least one operation.

2. Description of the Related Art

Nowadays, owing to a development of an image diagnosis apparatus utilizing nuclear magnetic resonance (MRI diagnosis apparatus), the location and size of a lesion can be recognized before a surgical operation is performed, and the surgical operation can be made efficiently and precisely.

Recently, an open-type MRI diagnosis apparatus having a space in its magnetic field generating apparatus portion has also been developed. Thus, a diagnosis is possible not only before a surgical operation is performed, but even during the surgical operation. Therefore, the surgical operation is expected to be made more precisely. Particularly in the field of neurosurgery, the expectation is great because the pressure inside a brain drops due to a craniotomy operation so that the position of a lesion may often be different from the position recognized before the surgical operation is performed.

In the field of neurosurgery, an operating microscope is generally used. A conventional operating microscope has the following problems when used with an open-type MRI diagnosis apparatus.

The conventional operating microscope has an arm and a microscope portion. The microscope portion is moved to shift the observed position, and focusing on the observed position is effectuated. In the conventional operating microscope, magnetic materials are used for the arm and the microscope portion and the like. The magnetic materials disturb a magnetostatic field of the MRI diagnosis apparatus. Thus diagnosis during surgery becomes impossible. Further, an intense magnetic field of the MRI diagnosis apparatus attracts the magnetic materials and hinders the movement or fixing of the microscope portion.

Japanese Laid-Open Patent Application Publication No. 1-180508 discloses a variable magnification microscope whose magnification is varied by a motor. The motor disturbs a magnetostatic field of an MRI diagnosis apparatus so that a diagnosis during a surgical operation is impossible. Further, because the motor itself is made of a magnetic material, an intense magnetic field of the MRI diagnosis apparatus attracts the motor and hinders the movement or fixing of the microscope portion.

Japanese Patent Application KOKOKU Publication No. 6-48329 discloses a stereoscopic microscope in which focusing is made by a motor. The stereoscopic microscope has the same problems as those described above.

Japanese Patent Application KOKOKU Publication No. 3-21887 discloses a microscope moving apparatus of an operating microscope. The apparatus moves a microscope by a motor to shift its field of view. This also has the same problems as those described above.

Japanese Patent Application KOKOKU Publication No. 55-36116 discloses a position adjusting stand apparatus in which an electromagnet is provided to a mechanism for fixing a microscope portion at a particular position. The electromagnet disturbs a magnetic field of an MRI diagnosis apparatus. Further, the microscope portion is attracted by the intense magnetic field and cannot be moved or fixed.

SUMMARY OF THE INVENTION

In view of the above problems, an object of this invention is to provide an operating microscope which solves the problem that a diagnosis by an MRI diagnosis apparatus cannot be made during a surgical operation and the problem that it is difficult to move and fix a microscope portion, so that the operating microscope can secure its proper operations and functions under the MRI diagnosis apparatus by a manual operation or via a power system.

A further object of this invention is to provide an operating microscope which can secure its proper operations and functions under an MRI diagnosis apparatus via a power system even when a surgeon performs a surgical operation remotely, for example, from another room, in order that the MRI diagnosis apparatus and the surgeon will not influence each other.

An operating microscope of this invention comprises a base and a support coupled to the base. An arm has a proximal end portion rotatably and/or vertically movably coupled to the support, and a distal end portion. At least the distal end portion is formed of a non-magnetic material. A microscope portion is coupled to the distal end portion of the arm and includes a stereoscopic optical system for forming an image of an observed part. The microscope portion is formed of a non-magnetic material. The operating microscope also comprises a power means for operating the microscope portion or a part thereof, and an operation instructing means for instructing the power means to operate. The power means comprises a power generating portion for generating a pressure change or a positional change; a power output portion, formed of a non-magnetic material, for converting the pressure change or the positional change of the power generating portion into a power for operating the microscope portion or a part thereof; and a power transmitting means for transmitting the pressure change or the positional change from the power generating portion to the power output portion. The power transmitting means is formed of a non-magnetic material at least near the power output portion.

According to this invention, when a surgeon makes an input operation, the power generating portion is driven and its pressure change or positional change is transmitted by the power transmitting means, which is formed of a non-magnetic material at least near the power output portion, to the power output portion formed of a non-magnetic material. The power output portion converts the transmitted pressure change or positional change into a driving force necessary for varying the magnification, focusing, shifting the field of view, and fixing the position of the microscope. During these functions, the operating microscope is not affected by the magnetic influence of the MRI diagnosis apparatus.

DETAILED DESCRIPTION OF THE PREFERRED EMBODIMENTS

Figure 1:
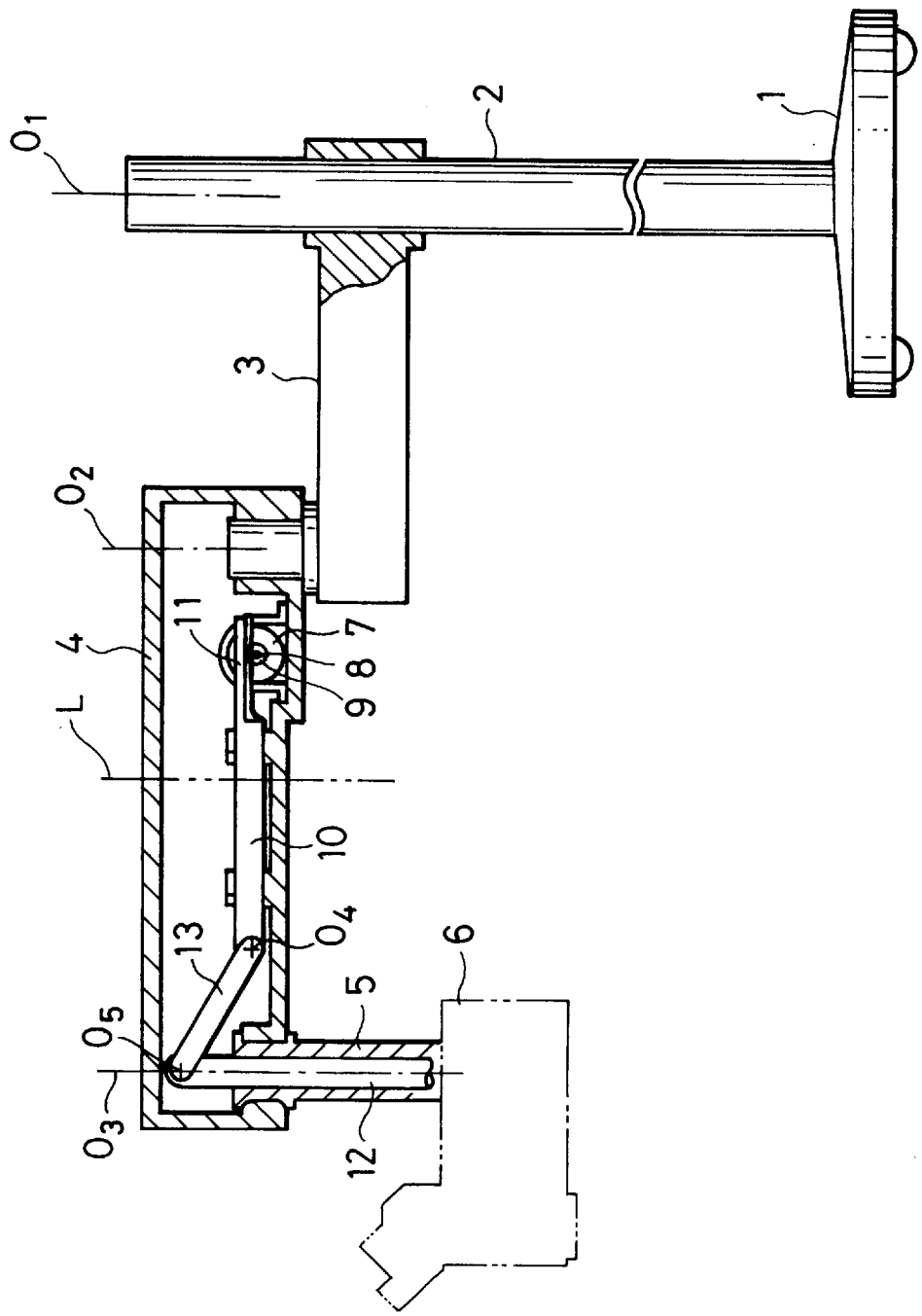
FIG. 1 is an illustration showing the structure of an operating microscope of a first embodiment of this invention.
Figure 2:
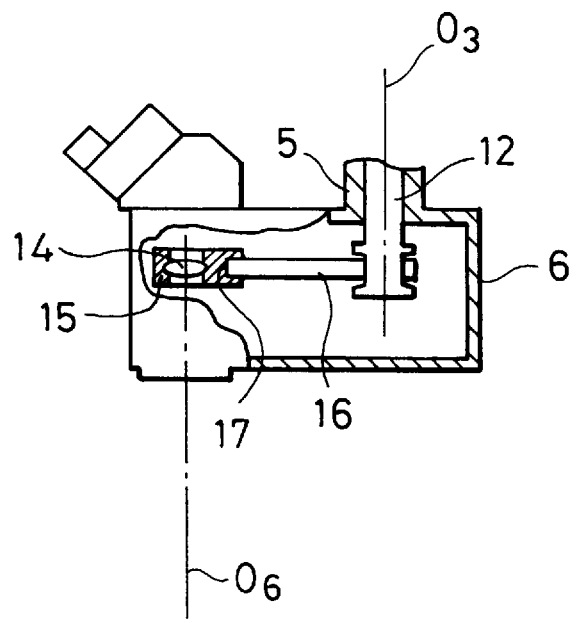
FIG. 2 is an illustration showing the structure of a microscope portion of the operating microscope of the first embodiment.
Figure 3:
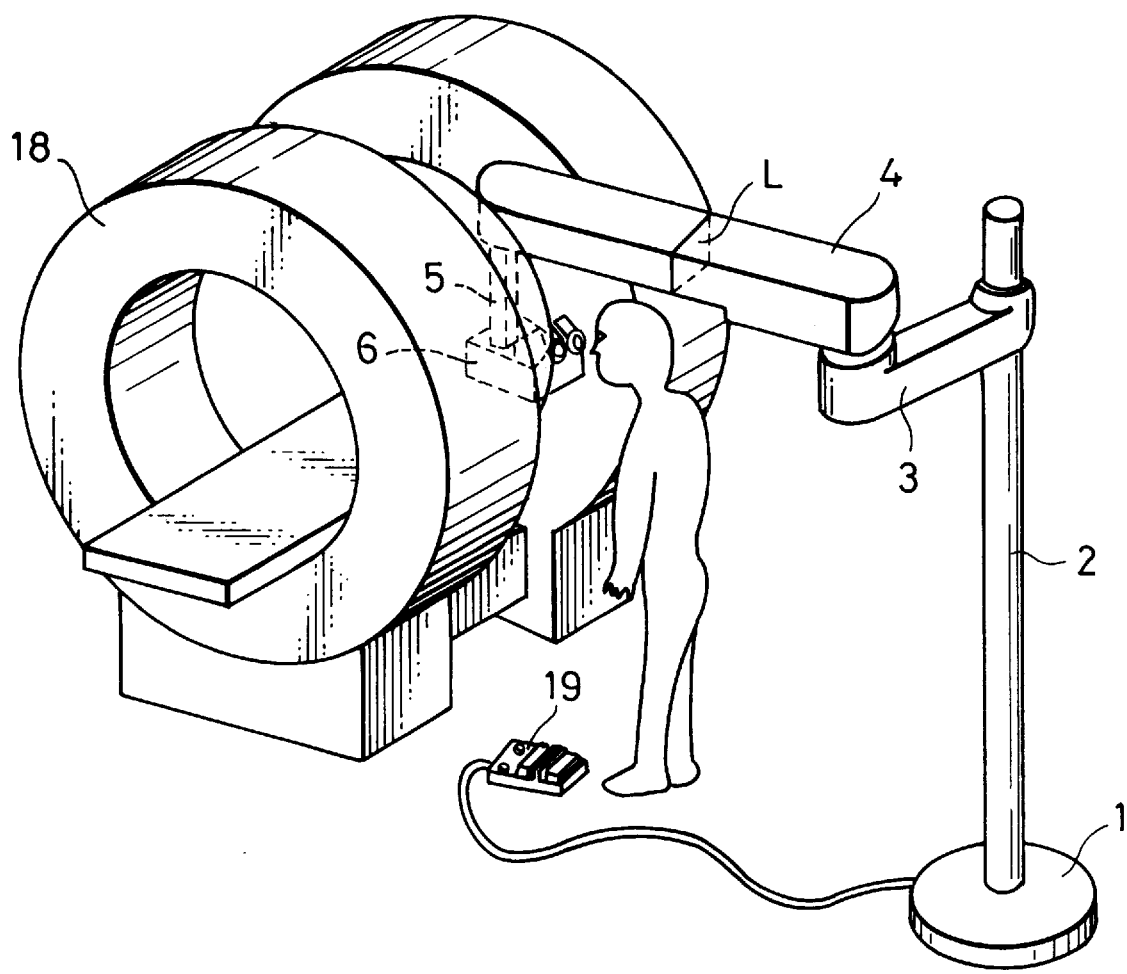
FIG. 3 is an outside view showing a combination of the operating microscope of the first embodiment and an MRI diagnosis apparatus.

Referring to FIGS. 1 to 3, a first embodiment of this invention will be described.

In FIG. 1, an operating microscope movable in an operating room has a base portion 1. A support 2 is vertically secured to the base portion 1. A first arm 3 is supported by the support 2 and can be moved up and down electromechanically along a vertical axis $O_1$ and rotated around the vertical axis $O_1$. A distal end portion of the first arm 3 is provided with a second arm 4 rotatably supported around an axis $O_2$ a shaft $O_2$ which is parallel with the vertical axis $O_1$. A distal end portion of the second arm 4 is similarly provided with a microscope portion mounting arm 5 rotatably supported around an axis $O_3$ which is parallel with the vertical axis $O_1$. A microscope portion 6 is secured to a lower end of the microscope mounting arm 5.

The second arm 4 is provided therein with a power generating portion for generating a positional change. That is, a motor 7 functioning as a driving source of the power generating portion is secured, and its rotating shaft 8 rotates around an axis which is perpendicular o the plane of the drawing. A pinion 9 is secured to the rotating shaft 8 of the motor 7.

Further, a power transmitting means is built in the second arm 4. That is, in the second arm 4, a first slide shaft 10 is provided so as to be slidable along the longitudinal axis of the second arm 4. One end portion of the first slide shaft 10 has a rack 11 which meshes with the pinion 9. The other end portion of the first slide shaft 10 is coupled to a second slide shaft 12 via a joint link 13.

The second slide shaft 12 is supported by the microscope mounting arm 5 so as to be slidable vertically along its axis $O_3$. One end of the joint link 13 is coupled to the distal end of the first slide shaft 10 so as to be rotatable around a rotational axis $O_4$ which is perpendicular to the plane of the drawing. The other end of the joint link 13 is coupled to an upper end of the second slide shaft 12 so as to be rotatable around a rotational axis $O_5$ which is perpendicular to the plane of the drawing. The above components compose the power transmitting means which transmits power (positional change) from the power generating portion to a power output portion which will be described below.

Non-magnetic materials are used for all of the members of the distal end portion of the power transmitting means, which is at the left (that is, on the microscope portion side) of the intermediate portion of the second arm 4, namely a border plane L orthogonal to the plane of the drawing. That is, at least the distal end portion of the power transmitting means (including the second arm 4) adjacent to the power output portion (described below) is formed of non-magnetic materials. Of course, the second arm 4 and all the members held by the second arm 4 may be formed of non-magnetic materials. The non-magnetic materials are, for example, metals (such as aluminum, titanium, and brass), resins (such as high polymer materials), or composite materials.

FIG. 2 shows the inside structure of the microscope portion 6 shown in FIG. 1. The microscope portion 6 is provided with a moving lens 14 of a variable magnification optical system. The moving lens 14 is supported by the lens frame 15 and movable back and forth along its optical axis $O_6$. The lens frame 15 is coupled to the second slide shaft 12 via an interlocking bar 16. One end of the interlocking bar 16 is supported rotatably around its axis $O_3$ with respect to the second slide shaft 12. The other end of the interlocking bar 16 is engaged with a hole 17 formed in the lens frame 15. As the second slide shaft 12 moves up and down, the moving lens 14 moves up and down with the lens frame 15. These members constitute the power output portion for operating an operating portion of the microscope portion 6 of the operating microscope by a positional change. Each member of the microscope portion 6 is formed of a non-magnetic material.

Referring to FIGS. 1 to 3, an operation of the first embodiment will be described.

A surgeon moves the base portion 1, namely the whole operating microscope such that the distal end portion beyond the border plane L can be used inside an MRI diagnosis apparatus 18. The microscope portion is moved by turning on moving switches of a foot switch 19 to electromechanically move the first arm 3 up and down with respect to the support 2, rotate the first arm 3 around the axis $O_1$ of the support 2, rotate the second arm 4 around the axis $O_2$ with respect to the first arm 3, and rotate the microscope portion mounting arm 5 around the axis $O_3$ with respect to the second arm 4.

A magnification varying operation is performed by the foot switch 19 or the like. When a surgeon turns on a magnification varying switch of the foot switch 19, the rotating shaft 8 and the pinion 9 of the motor 7 rotates. The rotation (positional change) causes the first slide shaft 10 to move in its axial direction via the rack 11 which meshes with the pinion 9. Further, the second slide shaft 12 is moved along the axis $O_3$, because the distance between the axes $O_4$ and $O_5$ is kept constant by the joint link 13. When the second slide shaft 12 moves along the axis $O_3$, the moving lens 14 of the variable magnification optical system moves along the optical axis $O_6$ via the interlocking bar 16 and the lens frame 15 to vary the magnification.

In this embodiment, the power generating portion comprises a motor 7. The power transmitting means comprises a slider and link mechanism which are formed by the first slide shaft 10, the joint link 13, and the second slide shaft 12. The power output portion comprises the interlocking bar 16. These portions and means cause the magnification varying operation of the microscope portion 6. Because all of the component members are rigid, their operation response is very good, their structures are simple, and their production costs are low.

Further, as described above, non-magnetic materials are used for all of the members of the distal end portion of the operating microscope, which is beyond the middle portion of the second arm 4, namely a border plane L in FIG. 3. Accordingly, when the microscope portion 6 is moved, these members will not influence the MRI diagnosis apparatus, and vice versa. Thus, the operating microscope can perform its proper functions smoothly, reliably, and stably.

In the first embodiment, the support 2 is secured to the base portion 1. However, the support 2 may be a supporting member suspended from a ceiling.

Figure 4:
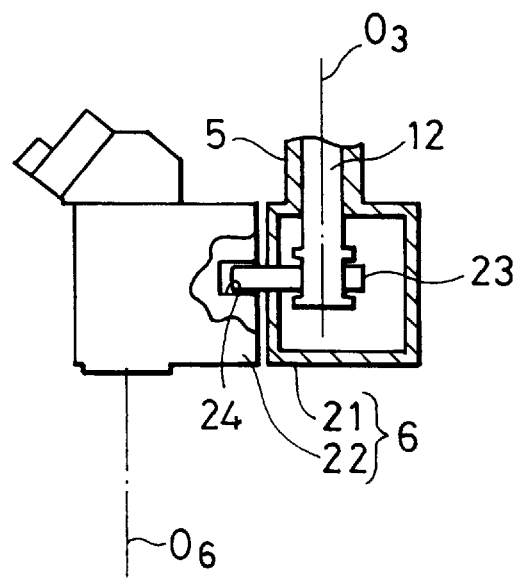
FIG. 4 is an illustration showing the structure of a microscope portion of an operating microscope of a second embodiment of this invention.

Referring to FIG. 4, an operating microscope according to a second embodiment of this invention will be described.

In the second embodiment, the operating microscope comprises a stand for holding a microscope portion 6. The stand is the same as that shown in FIG. 1 which comprises the base portion 1, the support 2, the first arm 3, and the second arm 4. Thus, its description is omitted.

The microscope portion 6 of the second embodiment is constructed as shown in FIG. 4. The microscope portion 6 comprises a fixed portion 21 secured to a microscope mounting arm 5, and a moving portion 22. The moving portion 22 of the microscope portion 6 incorporates an observation optical system (not shown) and is supported so as to be movable along an optical axis $O_6$ with respect to the fixed portion 21. For that purpose, the moving portion 22 of the microscope portion 6 is coupled to a second slide shaft 12 in the fixed portion 21 by an interlocking bar 23. That is, one end of the interlocking bar 23 is supported on the lower end portion of the second slide shaft 12 so as to be rotatable around an axis $O_3$. The other end of the interlocking bar 23 is engaged with a hole 24 of the moving portion 22. The interlocking bar 23 forms a power output portion.

Next, an operation of the second embodiment will be described.

A focusing operation is performed by the foot switch 19 of FIG. 3 or the like, as in the first embodiment. When a surgeon turns on the focusing switch of the foot switch 19, as in the first embodiment, the second slide shaft 12 moves along the axis $O_3$, and the moving portion 22 incorporating the observation optical system moves along the optical axis $O_6$ for focusing.

With respect to the driving operation for focusing, the same effects as those of the first embodiment can be obtained.

Figure 5:
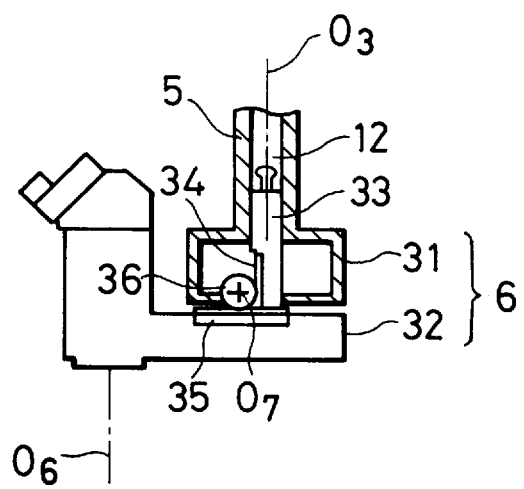
FIG. 5 is an illustration showing the structure of a microscope portion of an operating microscope of a third embodiment of this invention.

Referring to FIG. 5, an operating microscope according to a third embodiment of this invention will be described.

In the third embodiment, the operating microscope has the same stand for holding a microscope portion 6 as that of the first embodiment shown in FIG. 1. Therefore, its description is omitted.

FIG. 5 shows the structure of the microscope portion 6. A fixed portion 31 of the microscope portion 6 is secured to a microscope portion mounting arm 5. A moving portion 32 of the microscope portion 6 incorporates an observation optical system (not shown). The moving portion 32 is supported movably with respect to the fixed portion 31 in a direction perpendicular to an optical axis $O_6$.

A third slide shaft 33 is coupled to a second slide shaft 12 so as to be rotatable around an axis $O_3$. A rack 34 is formed in an end portion of the third slide shaft 33. A rack 35 is secured to an upper surface of the moving portion 32. A pinion 36 meshes with the rack 34 of the third slide shaft 33 and the rack 35 of the moving portion 32 to couple them together. The pinion 36 is supported rotatably with respect to the fixed portion 31 around an axis $O_7$ which is perpendicular to the plane of the drawing.

Next, an operation of the third embodiment will be described.

An operation for shifting the field of view is performed by the foot switch 19 shown in FIG. 3 or the like, as in the first embodiment. When a surgeon turns on a field-of-view shifting switch of the foot switch 19, as in the first embodiment, the second slide shaft 12 moves along the axis $O_3$ together with the third slide shaft 33. When the third slide shaft 33 moves, the moving portion 32 is moved in a direction perpendicular to the optical axis $O_6$ via the rack 34 formed in the end portion of the third slide shaft 33, the pinion 36, and the rack 35. Thus, the field of view is shifted.

With respect to the driving operation for shifting the field of view, the same effects as those of the first embodiment can be obtained.

Figure 6:
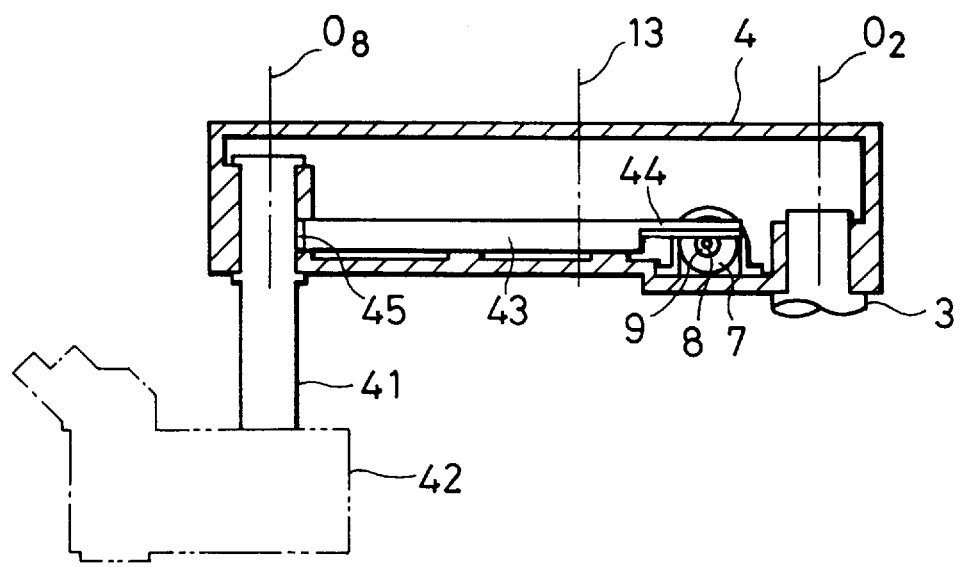
FIG. 6 is an illustration showing the structure of an arm portion of an operating microscope of a fourth embodiment of this invention.

Referring to FIG. 6, an operating microscope according to a fourth embodiment of this invention will be described.

In the fourth embodiment, a stand for holding a microscope portion 6 is the same as that of the first embodiment shown in FIG. 1. Therefore, its description is omitted.

In FIG. 6, a microscope portion mounting arm 41 is supported by a second arm 4 rotatably around an axis $O_8$ which is parallel to the vertical axis $O_1$. A microscope portion 42 is secured to the microscope mounting arm 41. A slide shaft 43 is supported within a second arm 4 so as to be slidable in its axial direction.

The proximal end portion of the slide shaft 43 is provided with a rack 44 which meshes with a pinion 9. A braking pad 45 is secured to the other end portion of the slide shaft 43. The braking pad 45 abuts the peripheral surface of the microscope mounting arm 41.

Next, an operation of the fourth embodiment will be described.

An operation for fixing or releasing the microscope portion 42 to or from the second arm 4 is performed by the foot switch 19 of FIG. 3 or the like. When a surgeon turns on a fixing switch or a releasing switch of the foot switch 19, as in the first embodiment, the pinion 9 rotates. The rotation causes the slide shaft 43 to move in its axial direction via the rack 44 which meshes with the pinion 9. The braking pad 45 secured to the slide shaft 43 is pushed against or separated from the outer peripheral surface of the microscope portion mounting arm 41 to perform the fixing or releasing.

With this structure, the microscope portion 42 can be fixed, and the same effects as those of the first embodiment can also be achieved.

Referring to FIGS. 7 to 10, a fifth embodiment of this invention will be described.

In the fifth embodiment, a microscope portion 67 is the same as that of the first embodiment. Therefore, its description is omitted.

Figure 7:
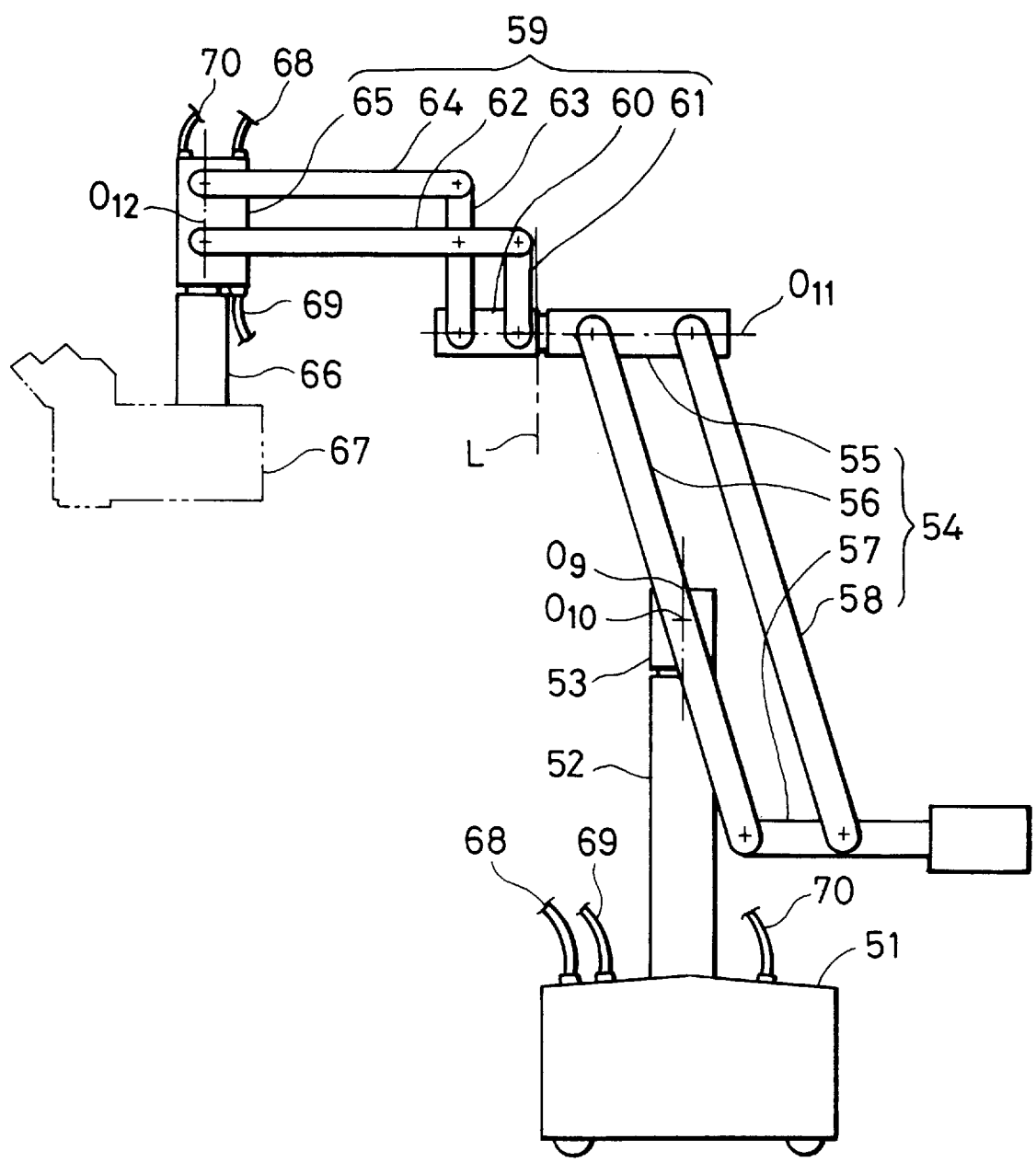
FIG. 7 is an elevational view showing the structure of an operating microscope of a fifth embodiment of this invention.

In FIG. 7, an operating microscope movable in an operation room comprises a base portion 51. A support 52 is fixed to the base portion 51. A link seat 53 is supported by the support 52 rotatably around a vertical axis $O_9$. A parallelogram link 54 has links 55, 56, 57 and 58 coupled together at their respective end portions so that they can rotate around axes which are perpendicular to the plane of the drawing. The parallelogram link 54 is supported by the link seat 53 so as to be rotatable around an axis $O_{10}$ which is perpendicular to the plane of the drawing. A second parallelogram link 59 has links 60, 61, 62, 63, 64, and 65 coupled together at their respective end portions and intermediate points of the links 62 and 63 so that they can rotate around axes which are perpendicular to the plane of the drawing. The second parallelogram link 59 is supported by the first parallelogram link 54 so as to be rotatable around an axis $O_{11}$.

A microscope portion mounting arm 66 is supported by the second parallelogram link 59 so as to be rotatable around an axis $O_{12}$. A microscope portion 67 is secured to the microscope portion mounting arm 66. The base portion 51 is coupled to the link 65 of the second parallelogram link 59 by a plurality of flexible wire transmitting mechanisms 68, 69, and 70.

Non-magnetic materials are used for all of the members of the distal end portion of the operating microscope (including the wire transmitting mechanisms 68, 69, and 70, and the microscope portion 67), which is beyond a border plane L perpendicular to the plane of the drawing, that is, on the side of the microscope portion 67. Of course, all of the members of the operating microscope (including the first parallelogram link 54 positioned above the base portion 51) may be formed of non-magnetic materials.

Figure 8:
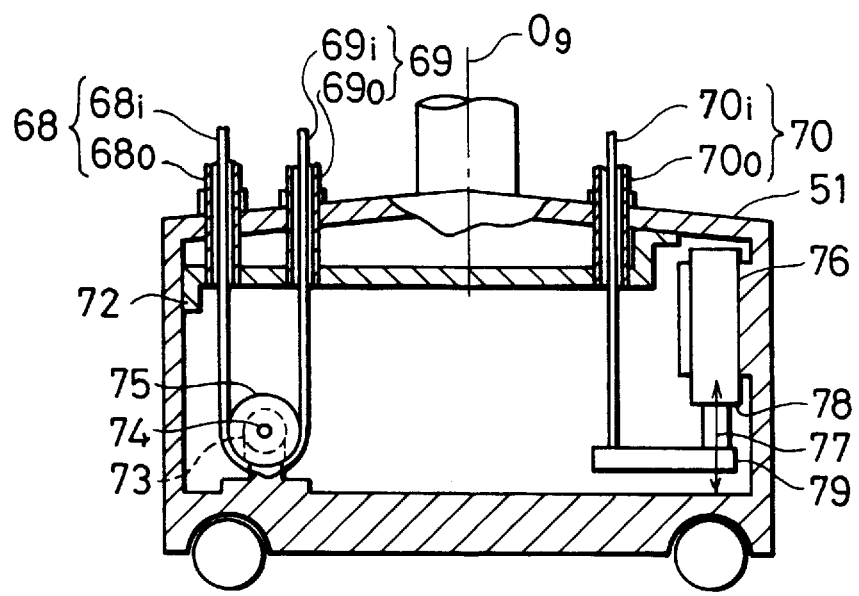
FIG. 8 is a cross-sectional view showing the structure of a base portion of the operating microscope of the fifth embodiment.
Figure 9:
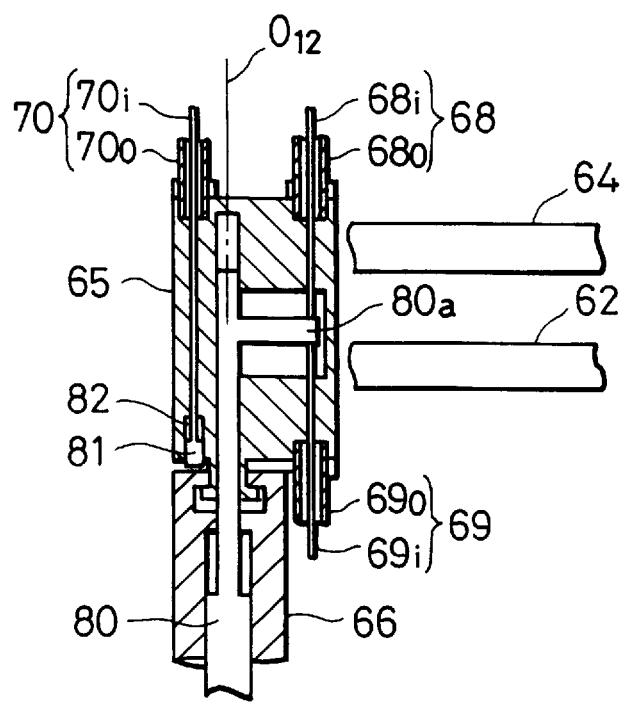
FIG. 9 is a cross-sectional view showing the structure of a distal end link portion of the operating microscope of the fifth embodiment.

Next, referring to FIGS. 8 to 9, the structures of the wire transferring mechanism 68, 69, and 70 as a power transmitting means is described.

FIG. 8 shows the inside structure of the base portion 51 and the wire transmitting mechanisms 68, 69, and 70. Numerals $68_i$, $69_i$, and $70_i$ denote inners of the wire transmitting mechanisms 68, 69, and 70, respectively. Numerals $68_o$, $69_o$, $70_o$, denote outers of the wire transmitting mechanisms 68, 69, and 70, respectively. The inners $68_i$, $69_i$, and $70_i$ are slidably inserted through the outers $68_o$, $69_o$, and $70_o$, respectively, and are guided separately.

End portions of the outers $68_o$, $69_o$, and $70_o$, are secured to a fixed seat 72 of the base portion 51. In the base portion 51, a motor 73 functioning as a power generating portion is secured. The motor 73 has a rotating shaft 74 which rotates around an axis perpendicular to the plane of the drawing. A pulley 75 is secured to the rotating shaft 74 of the motor 73. End portions of the inners $68i$ and $69i$ are secured to the outer periphery of the pulley 75.

A push-pull solenoid 76 is another power generating portion fixed in the base portion 51. The push-pull solenoid 76 has a shaft 78 which advances and retracts in the direction of an arrow 77. An inner seat 79 is secured to one end of the shaft 78. One end portion of the inner $70_i$ is secured to the inner seat 79.

FIG. 9 shows the structure of the wire transmitting mechanisms 68, 69, and 70 in a link 65. The other ends of the outers $68_o$ and $70_o$ are secured to the link 65. A slide shaft 80 is supported slidably along the axis $O_{12}$ with respect to the microscope portion mounting arm 66.

A securing arm 80a is provided to the slide shaft 80 so as to protrude from the slide shaft 80. The other end portions of the inners $68_i$ and $69_i$ are secured to opposite side surfaces of the securing arm 80a. A brake pad 81 is secured to the inner $70_i$ and engaged with and held by the link 65. The brake pad 81 is pressed against the microscope portion mounting arm 66 by a spring 82.

Next, referring to FIGS. 7 to 10, an operation of the fifth embodiment will be described.

A surgeon moves the base portion 51, namely the whole operating microscope so that its distal end portion beyond the border plane L is used with an MRI diagnosis apparatus 18. The microscope portion 67 is moved by performing the following operations: rotation of the link seat 53 around the axis $O_9$ with respect to the support 52, rotation of the first parallelogram link 54 around the axis $O_{10}$ with respect to the link seat 53, deformation of the first parallelogram link 54, rotation of the second parallelogram link 59 around the axis $O_{11}$ with respect to the first parallelogram link 54, deformation of the second parallelogram link 59, and rotation of the microscope portion mounting arm 66 around the axis $O_{12}$ with respect to the second parallelogram link 59.

A magnification varying operation, a focusing operation, and a field-of-view shifting operation are performed by using a foot switch 19. When the surgeon turns on switches of the foot switch 19, the rotating shaft 74 of the motor 73 and the pulley 75 inside the base portion 51 rotate. This rotation is converted to a relative movement of the inners $68_i$ and $69_i$ secured to the pulley 75 with respect to their outers $68_o$ and $69_o$ and the relative movement is transmitted to the link 65. The relative movement transmitted to the link 65 is converted to a movement of the slide shaft 80, to which the inners $68i$ and $69i$ are secured, along the axis $O_{12}$. The movement of the slide shaft 80 along the axis $O_{12}$ has the same function as that of the second slide shaft 12 moving along the axis $O_3$ in the first, second, and third embodiments. Therefore, as described in the first, second, and third embodiments, the magnification varying, focusing, and field-of-view shifting operations are performed.

An operation for fixing or releasing the microscope portion 67 to or from the second parallelogram link 59 is performed by the foot switch 19. When the surgeon turns on a fixing switch or a releasing switch of the foot switch 19, the shaft 78 of the push-pull solenoid 76 and the inner seat 79 inside the base portion 51 advance and retract. The advancing and retracting movement is converted to a relative movement of the inner 70$_i$ secured to the inner seat 79 with respect to its outer 70$o$ and the relative movement is transmitted to the link 65. Owing to the relative movement transmitted to the link 65, the brake pad 81 secured to the inner 70$_i$ and pressed against by the spring 82 is separated from or pressed against the upper surface of the microscope portion mounting arm 66 for releasing or fixing.

In this embodiment, the power generating portion comprises the motor 73 and the push-pull solenoid 76, and the power transmitting means comprises wire transmitting mechanisms 68, 69, and 70. Therefore, while the microscope portion 67 can move more freely, operation response is very good. In addition, the structure is simple and the production costs are low. In this embodiment, only the fixing of the microscope portion 67 to the second parallelogram link 59 is described. However, the fixing of the second parallelogram link 59 to the first parallelogram link 54 can be implemented in the same way.

Figure 11:
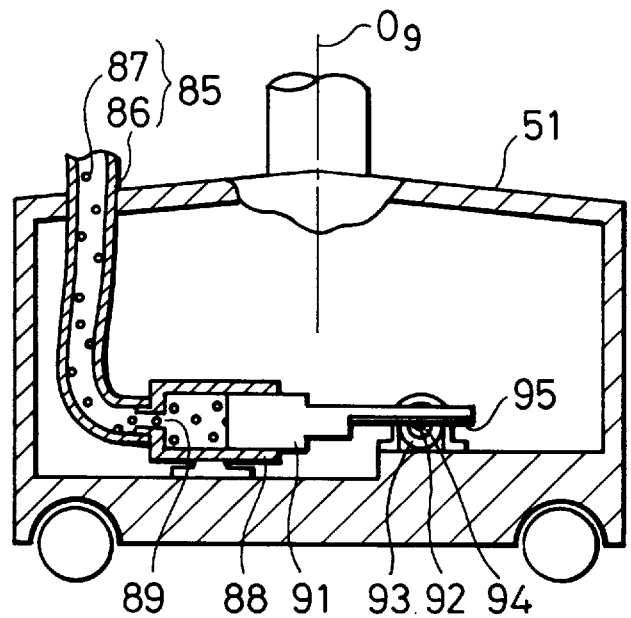
FIG. 11 is a cross-sectional view showing the structure of a base portion of an operating microscope of a sixth embodiment of this invention.
Figure 12:
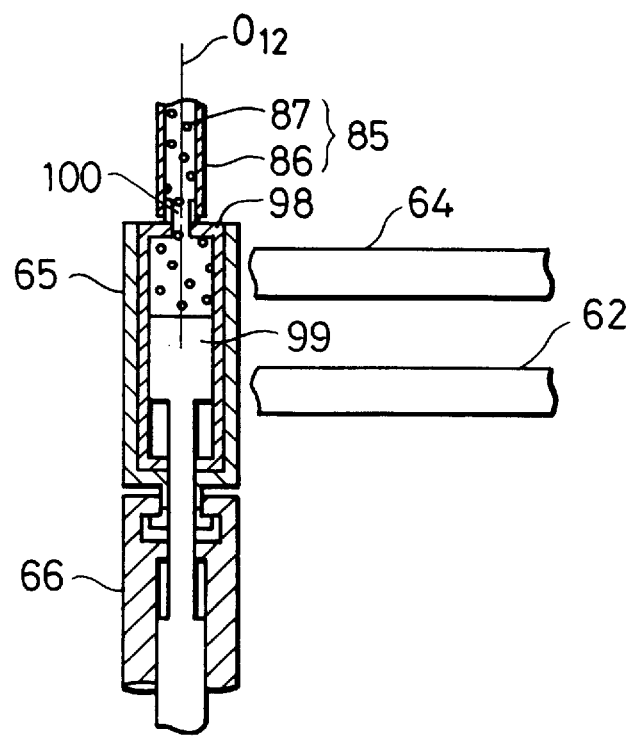
FIG. 12 is a cross-sectional view showing the structure of a distal end link portion of the operating microscope of the sixth embodiment.

Referring to FIGS. 11 and 12, an operating microscope according to a sixth embodiment of this invention will be described.

The sixth embodiment is the same as the fifth embodiment, except for the wire transmitting mechanisms shown in FIG. 7 and the power generating portion and the power output portion provided at both ends of the wire transmitting mechanisms 68, 69, and 70. Therefore, the description of the common parts is omitted.

FIG. 11 shows the structure of a base portion 51 and a hydraulic transmission mechanism 85. The hydraulic transmission mechanism 85 comprises an oil tube 86 made of a resin which is a flexible non-magnetic material. The oil tube 86 is filled with a non-magnetic oil 87, which flows freely. Thus, the hydraulic transmission mechanism 85 is formed of non-magnetic materials. One end of the oil tube 86 of the hydraulic transmission mechanism 85 is connected to an oil inlet and outlet 89 of a first oil case 88 which is secured inside the base portion 51. The oil 87 in the oil tube 86 flows in and out of the first oil case 88 through the oil inlet and outlet 89.

A piston 91 is fitted in the first oil case 88 fluid-tightly and slidably. The first oil case 88 is a cylinder for the piston 91. Inside the base portion 51, a motor 93 is secured. The motor 93 has a rotating shaft 92 which rotates around an axis perpendicular to the plane of the drawing. A pinion 94 is secured to an end portion of the rotating shaft 92. A rack 95 is formed in an end portion of the piston 91 so as to mesh with the pinion 94.

FIG. 12 shows the inside structure of the link 65 and a distal end portion of the hydraulic transmission mechanism 85. A second oil case 98 is secured to the link 65. A slide shaft 99 is fitted in the second oil case 98 fluid-tightly and slidably. The second oil case 98 is a cylinder for the slide shaft 99 functioning as a piston.

The second oil case 98 is provided with a second oil inlet and outlet 100. The other end of the oil tube 86 is secured to the second oil inlet and outlet 100. The oil 87 inside the oil tube 86 flows in and out of the second oil case 98 through the second oil inlet and outlet 100.

The members of the link 65 and the microscope portion 67 are made of non-magnetic materials.

Next, referring to FIGS. 11 to 12, an operation of the sixth embodiment will be described.

A magnification varying operation, a focusing operation, and a field-of-view shifting operation are performed by using the foot switch 19 (see FIG. 10) or the like. When a surgeon turns on switches of the foot switch 19, the rotating shaft 92 of the motor 93 and the pinion 94 inside the base portion 51 rotate. The rotation moves the piston 91 via the rack 95 which meshes with the pinion 94. The oil 87 flows from the oil case 88 to the oil tube 86 or vice versa via the first oil inlet and outlet 89 and the movement of the oil 87 is transmitted to the link 65. The movement of the oil 87 transmitted to the link 65 is translated into the movement, along an axis $O_{12}$, of the slide shaft 99 engaging with the second oil case 98 as the oil 87 flows in the second oil case 98 from the oil tube 86 or vice versa through the second oil inlet and outlet 100. The slide shaft 99 functions in the same way as the slide shaft 80 of the fifth embodiment for magnification varying, focusing, and field-of-view shifting.

In this embodiment, the hydraulic transmission mechanism 85 constitutes a power transmitting means, which is very flexible. Accordingly, the movement of the microscope portion 67 is not hindered. Further, because no transmission error will occur, the magnification varying speed and the like can be easily controlled from the power generating portion. In the same way as in the fifth embodiment, the movement of the slide shaft 99 can be used for fixing or releasing the microscope portion 67.

Figure 13:
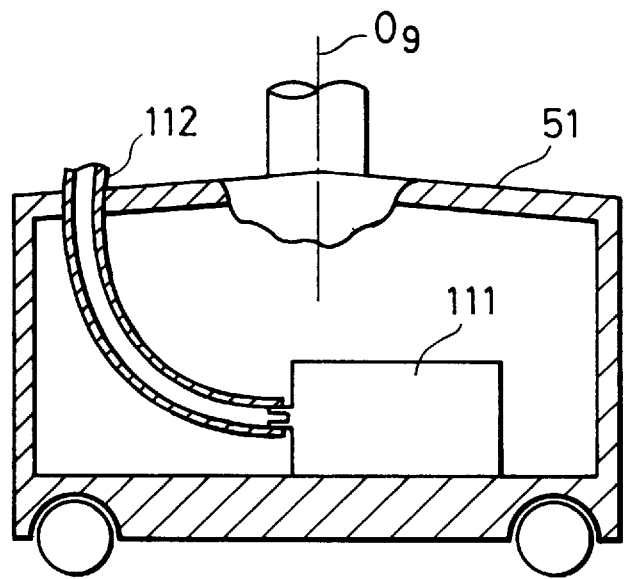
FIG. 13 is a cross-sectional view showing the structure of a base portion of an operating microscope of a seventh embodiment of this invention.
Figure 14:
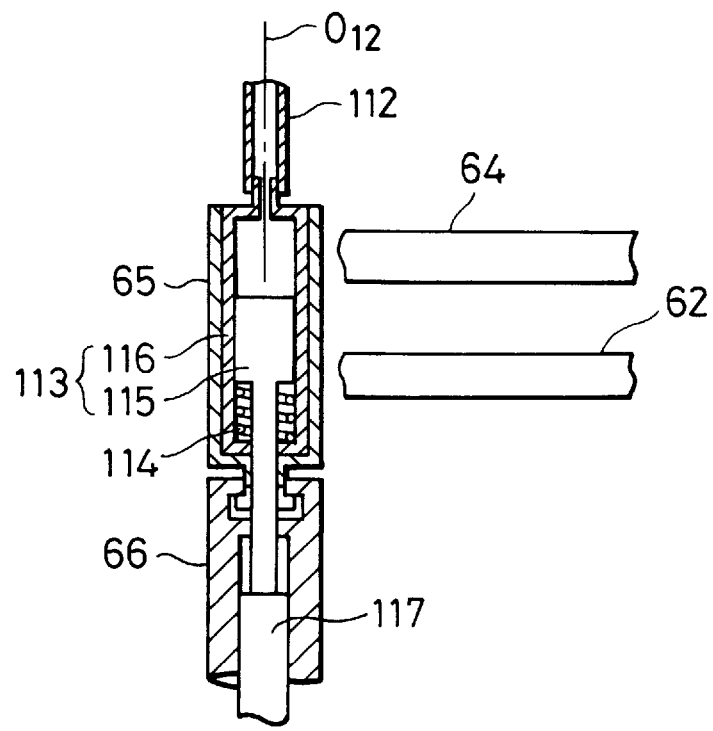
FIG. 14 is a cross-sectional view showing the structure of a distal end link portion of the operating microscope of the seventh embodiment.

Referring to FIGS. 13 and 14, an operating microscope according to a seventh embodiment of this invention will be described.

The seventh embodiment is the same as the fifth embodiment, except for the wire transmitting mechanisms 68, 69, and 70 shown in FIG. 7 and the power generating portion and the power output portion provided at both ends of the wire transmitting mechanisms 68, 69, and 70. Therefore, the description of the common parts is omitted.

FIG. 13 shows the inside structure of a base portion 51 corresponding to that of FIG. 7 of the fifth embodiment An air compressor 111 is secured to the inside of the base portion 51. One end of an air tube 112 formed of a flexible non-magnetic material is connected to a discharge opening of the air compressor 111. Alternatively, only the distal end portion of the air tube 112 may be formed of a non-magnetic material.

FIG. 14 shows the structure of a link 65 corresponding to that of FIG. 7. An air cylinder 113 is secured to the link 65. The other end of the air tube 112 is connected to the air cylinder 113. A piston 115 is slidably received in a pressure chamber 116 of the air cylinder 113. The pressure chamber 116 is provided with a spring 114 for urging the piston 115 in order to discharge air from the pressure chamber 116. The piston 115 is secured to a slide shaft 117 which is movable along an axis $O_{12}$. The members of the air tube 112 and the link 65 are formed of non-magnetic materials.

Next, referring to FIGS. 13 and 14, an operation of the seventh embodiment will be described.

A magnification varying operation, a focusing operation, and a field-of-view shifting operation are performed by using the foot switch 19 (see FIG. 10) or the like. When a surgeon turns on a switch on the foot switch 19, air pressure inside the air compressor 111 changes. The change of pressure is transmitted to the air cylinder 113 via the air tube 112. The change of pressure of the pressure chamber 116 is converted to the movement, along the axis $O_{12}$, of the piston 115 urged by the spring 114 to discharge air from the pressure chamber 116, and the slide shaft 117 secured to the piston 115.

Since the slide shaft 117 has the same structure as that of the slide shaft 80 of the fifth embodiment, the magnification varying, focusing and field-of-view shifting are performed.

In the seventh embodiment, the air tube 112 transmitting the pressure change constitutes a power transmitting means. Thus, it is lightweight, and inertial force during the movement of the microscope portion 67 will not increase. The same effect can be achieved by replacing the air compressor 111 inside the base portion 51 with an air source provided in the operation room and by incorporating only a vale for pressure adjustment in the base portion 51.

Further, in the same way as in the fifth embodiment, the movement of the slide shaft 117 can be used for fixing or releasing the microscope portion 67.

Figure 15:
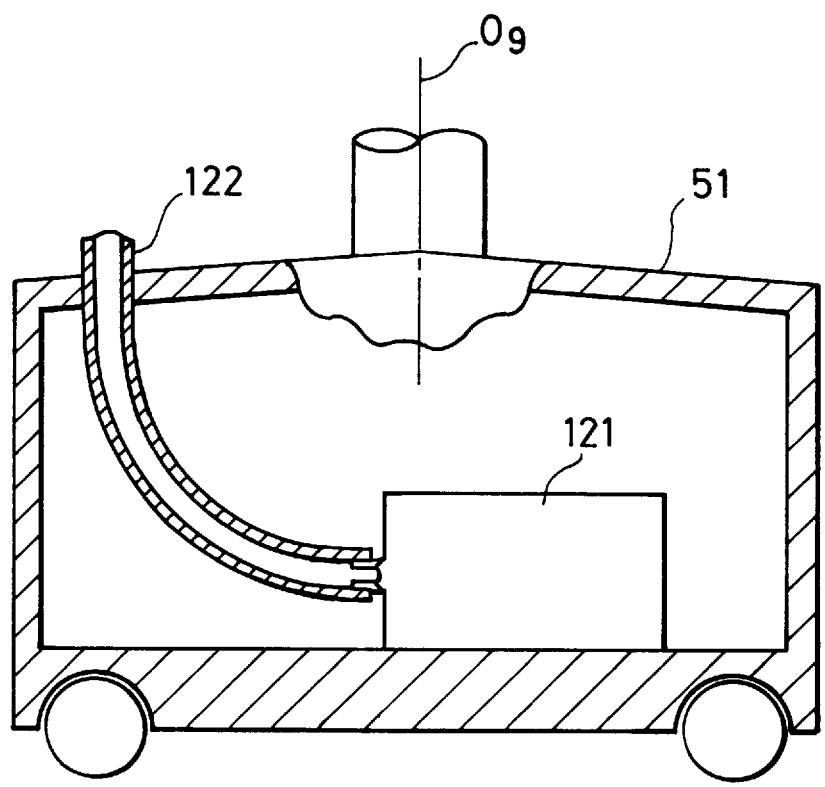
FIG. 15 is a cross-sectional view showing the structure of a base portion of an operating microscope of an eighth embodiment of this invention.
Figure 16:
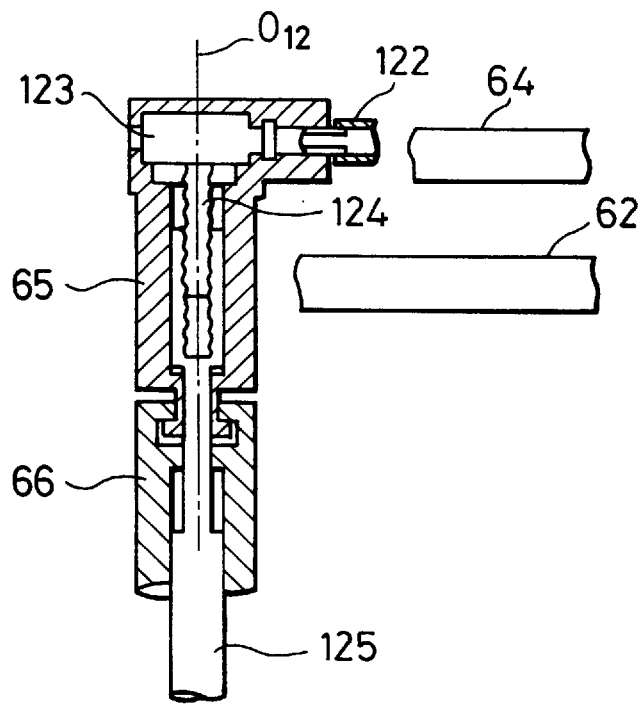
FIG. 16 is a longitudinal section showing the structure of a distal end link portion of the operating microscope of the eighth embodiment.
Figure 17:
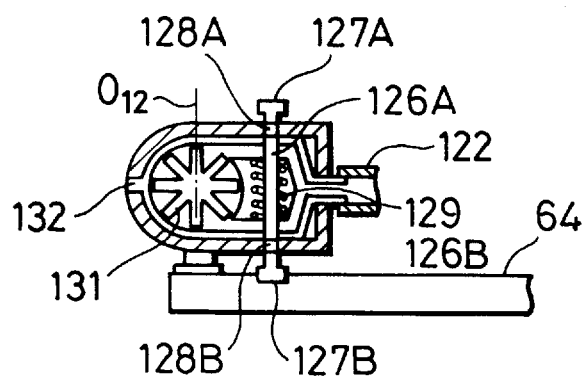
FIG. 17 is a cross-sectional view showing the structure of the distal end link portion of the operating microscope of the eighth embodiment.

Referring to FIGS. 15 to 17, an operating microscope according to an eighth embodiment of this invention will be described.

The eighth embodiment is the same as the fifth embodiment, except for the wire transmitting mechanisms 68, 69, and 70 shown in FIG. 7 and the power generating portion and the power output portion provided at both ends of the wire transmitting mechanisms 68, 69, and 70. Therefore, the description of the common parts is omitted.

FIG. 15 shows the structure of a base portion 51 corresponding to that of FIG. 7. An air pump 121 is fixed inside the base portion 51. One end of an air tube 122 formed of a flexible non-magnetic material is connected to an discharging opening of the air pump 121.

FIG. 16 shows the structure of a link 65 corresponding to that of FIG. 7. An air turbine 123 is secured to the link 65. The other end of the air tube 122 is connected to the air turbine 123. A rotating shaft 124 of the air turbine 123 rotates around an axis $O_{12}$. A male thread is formed on the outer periphery of the rotating shaft 124. Further, a slide shaft 125 movable along the axis $O_{12}$ is provided in the link 65. A female thread engaging with the male thread is formed on the inner periphery of the slide shaft 125.

FIG. 17 shows the structure shown in FIG. 16 which is viewed from above. The air tube 122 is connected to the air turbine 123. The air tube 122 is divided into two passages. The passages are provided with valves 126A and 126B, respectively. Respective outlet openings of the passages face the air turbine 123. Operation buttons 127A and 127B are provided in order to open and close the valves 126A and 126B from the outside.

The valves 126A and 126B operated by the operating buttons 127A and 127B are provided with through holes 128A and 128B for opening, respectively. By pushing in the operating buttons 127A and 127B, passages for the valves 126A and 126B are opened. A spring 129 is for returning the valves 126A and 126B.

Blades 131 are secured to the rotating shaft 124 of the air turbine 123. The air turbine 123 is provided with an air outlet 132. Also in this embodiment, the air tube 122 and the link 65 are made of non-magnetic materials.

Next, referring to FIGS. 15 to 17, an operation of the eighth embodiment will be described.

A magnification varying operation, a focusing operation, and a field-of-view shifting operation are performed by operating the operating buttons 127A and 127B which opens the valves 126A and 126B. When an operator operates the operating button 127A or 127B, the valve 126A or 126B is opened, and air is fed from the air pump 121 into the air turbine 123. The air fed into the air turbine 123 rotates the rotating shaft 124 via the blades 131 in either direction depending on which of the valves 126A and 126B has been opened. Then, the air is discharged from the air outlet 132. The rotation of the rotating shaft 124 is converted to a movement of the slide shaft 125 along the axis $O_{12}$, owing to the engagement of the male thread formed on the rotating shaft 124 with the female thread formed in the slide shaft 125. The slide shaft 125 functions in the same way as the slide shaft 80 of the fifth embodiment. Therefore, the magnification varying, focusing, and field-of-view shifting are performed.

In the eighth embodiment, the air turbine 123 constitutes a power output portion, in which a rotating movement is generated. Therefore, the power output portion can be used in place of a motor, made of a magnetic material, of an conventional operating microscope.

The movement of the slide shaft 125 can be used for fixing or releasing the microscope portion 67, as in the fifth embodiment.

Referring to FIGS. 18 to 21, a ninth embodiment of this invention will be described.

Figure 18:
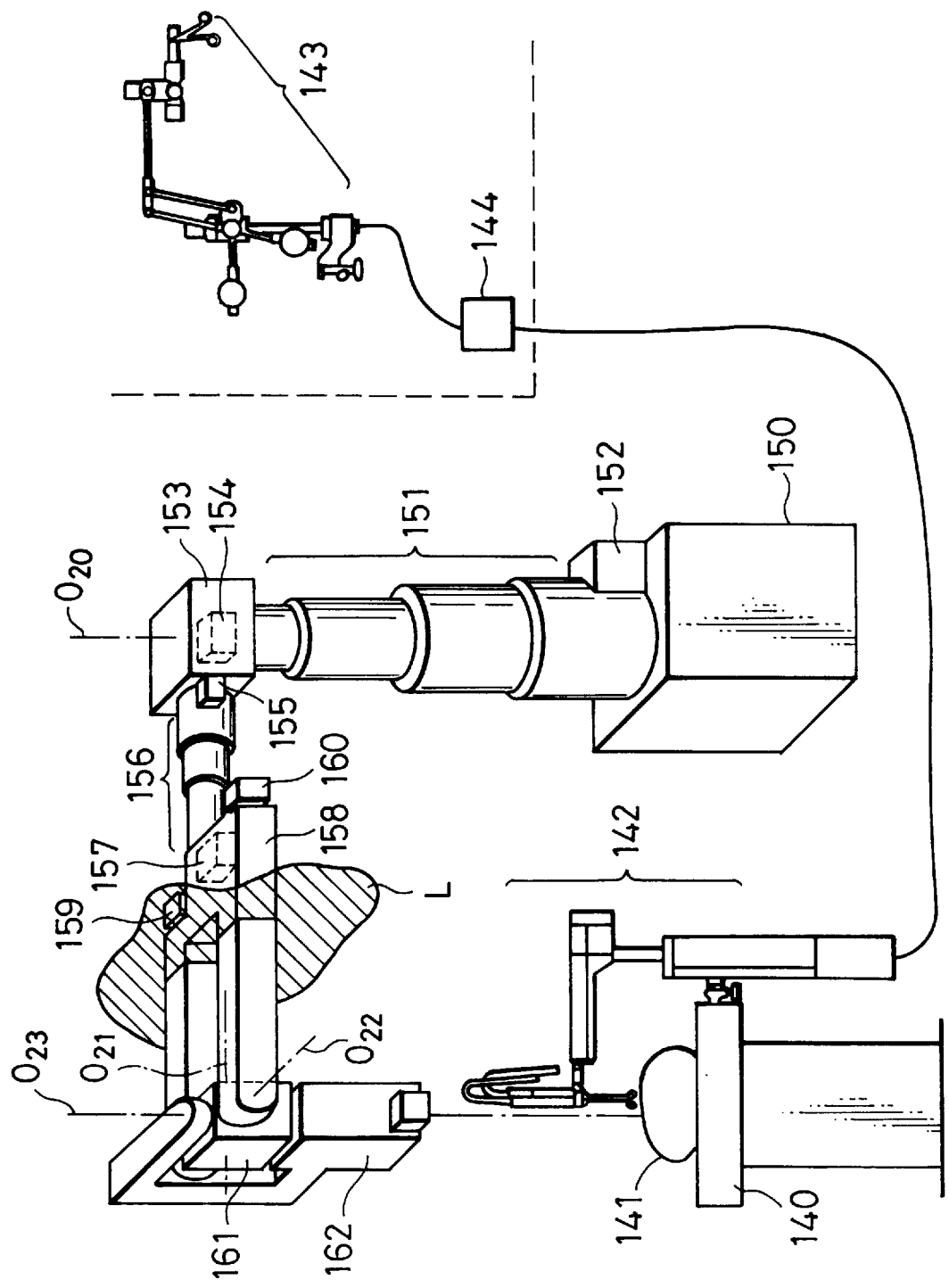
FIG. 18 is an illustration showing a whole system of a remotely operable operating microscope of a ninth embodiment of this invention, an operating table which is a part of an MRI diagnosis apparatus and to which a treatment manipulator is attached, and an operation manipulator for remotely operating the treatment manipulator.

FIG. 18 shows an operating microscope system according to the ninth embodiment, which is remotely controlled by a surgeon in a place remote from the magnetic field of an MRI diagnosis apparatus in order to perform an observation and a surgical operation.

An operating microscope can be moved in an operation room or fixed to the inside of the operation room, for example, to the floor or the ceiling. The operating microscope comprises a base portion 150, which is secured to a support 151 extendable in a vertical direction by a motor 152. An upper end of the support 151 is secured to a block 153 which can be rotated around a vertical axis $O_{20}$ by a motor 154. The block 153 is secured to one end of an arm 156 which can be extended and retracted in a horizontal direction by a motor 155. The other end of the arm 156 is coupled to a U-shaped arm 158 which can be rotated around a horizontal axis $O_{21}$ by a motor 157. Television cameras 159 and 160 described below pick up images of a portion to be surgically operated. Eyepieces can be substituted for the television cameras 159 and 160. An inclining block 161 is coupled to distal ends of the U-shaped arm 158. Owing to a rotation mechanism described below, the inclining block 161 is rotatable around an rotational axis $O_{22}$ perpendicular to the horizontal axis $O_{21}$. An image pick-up unit 162 is coupled to the inclining block 161. Owing to a rotation mechanism described below, the image pick-up unit 162 is rotatable around an rotational axis $O_{23}$ perpendicular to the rotational axis $O_{21}$ and $O_{22}$.

All of the members of the distal end portion of the operating microscope beyond a border plane L of FIG. 18, namely on the side of the image pick-up unit 162, are made of non-magnetic materials.

Next, referring to FIG. 18, an operating table 140 positioned in the MRI diagnosis apparatus (not shown), and the vicinity of the operating table 140 are described.

A patient 141 is lying on the operating table 140. Numerals 142 and 143 denote a treatment manipulator and an operation manipulator operated by a surgeon, respectively, as disclosed in Japanese Laid-Open Patent Application Publication No. 7-328014. A motor control unit 144 is connected to the treatment manipulator 142 and the operation manipulator 143. The operation manipulator 143 reads the information about the position and posture of the hand of the surgeon. The information is input to the motor control unit 144. Based on the information about the position and posture, the motor control unit 144 operates the treatment manipulator 142 for a specified amount. In this embodiment, the whole treatment manipulator 142 is formed of non-magnetic materials. The operation manipulator 143 and the motor control unit 144 are positioned in a control room described below where they will not affect the magnetic field of the MRI diagnosis apparatus.

Figure 19:
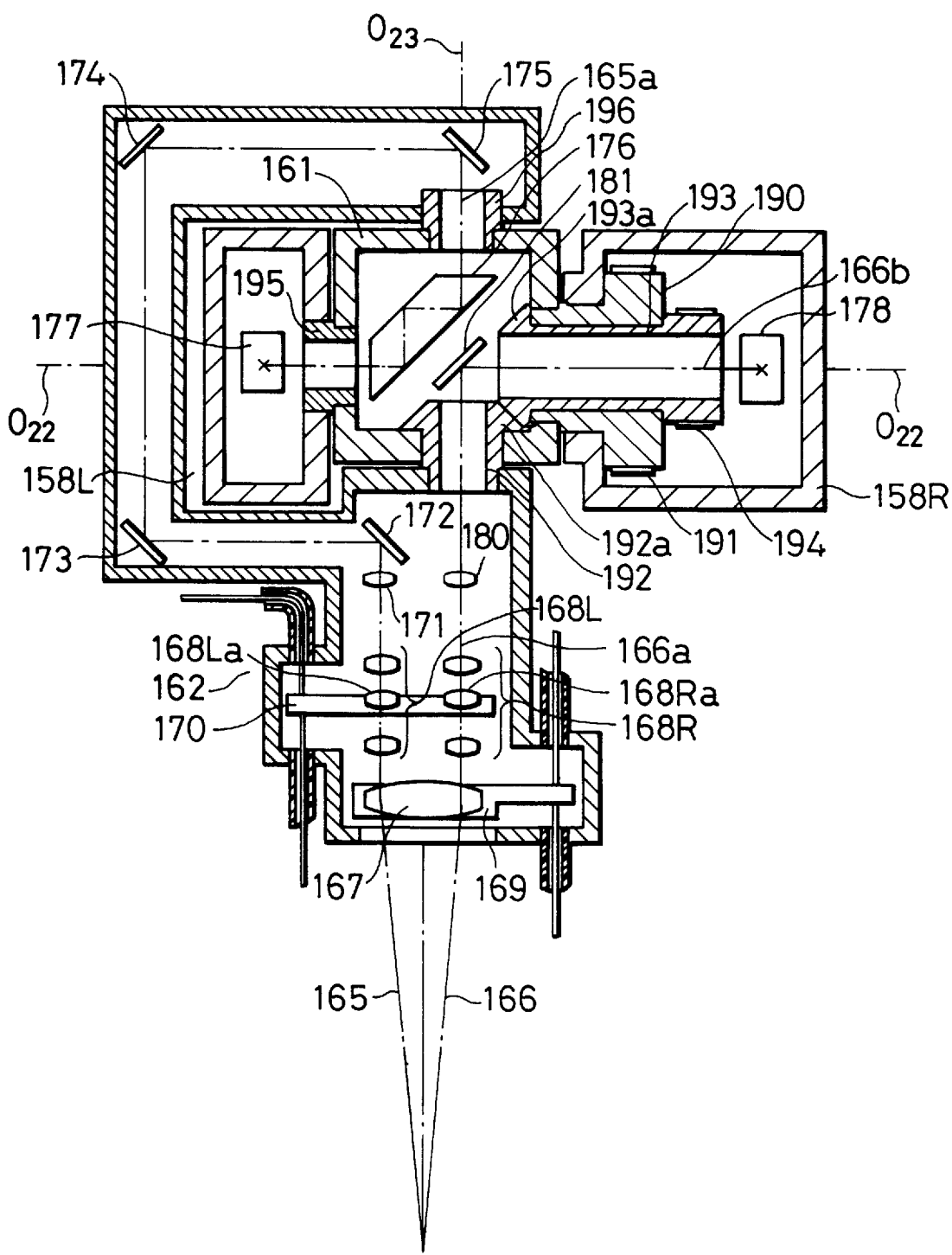
FIG. 19 is a cross-sectional view showing an image pick-up unit and a U-shaped arm of FIG. 18, taken in a plane containing rotational axes $O_{22}$ and $O_{23}$ of FIG. 18.

FIG. 19 is a cross-sectional view of the image pick-up unit 162 and the U-shaped arm 158 taken along the plane including the rotational axes $O_{22}$ and $O_{23}$.

Referring to FIG. 19, an imaging optical system is described.

On a left imaging optical axis 165 and a right imaging optical axis 166, there are arranged, in the order from the object side, an objective lens 167 and magnification varying lenses 168L and 168R. The magnification varying lens 168L is on the left side and the magnification varying lens 168R is on the right side. The objective lens 167 is supported by a lens frame 169 coupled to the image pick-up unit 162 and is advanceable and retractable along the left and right imaging optical axes 165 and 166. Moving lenses 168La and 168Ra are component elements of the magnification varying lenses 168L and 168R. The moving lenses 168La and 168Ra are supported by a lens frame 170 coupled to the image pick-up unit 162 and are advanceable and retractable along the left and right imaging optical axes 165 and 166. Transmission mechanisms for advancing and retracting the objective lens 167 and the moving lenses 168La and 168Ra have the same structure as that shown in FIGS. 8 and 9 for driving the slide shaft 80 in the fifth embodiment. Therefore, its description is omitted.

On the imaging optical axis 165 above the magnification varying lens 168L, a relay lens 171 and mirrors 172, 173, 174, and 175 are fixed to the image pick-up unit 162. An outgoing optical axis 165a leaving the mirror 175 coincides with the rotational axis $O_{23}$. A prism 176 is fixed to the inclined block 161. A mirror 177 is fixed to a left arm 158L of the U-shaped arm 158. Owing to the prism 176, the outgoing optical axis 165a coincides with the rotational axis $O_{22}$ and impinges on the mirror 177. Light leaving the mirror 177 reaches a television camera 159 via a prism 180L and an image forming lens 200L which are described below.

On the imaging optical axis 166 above the magnification varying lens 168R, a relay lens 180 is fixed to the image pick-up unit 162, and a mirror 181 is fixed to the inclining block 161. An imaging optical axis 166a between them coincides with the rotational axis $O_{23}$. An optical axis 166b reflected by the mirror 181 coincides with the rotational axis $O_{22}$ and impinges on a mirror 178 fixed to a right arm 158R of the U-shaped arm 158. Light leaving the mirror 178 reaches a television camera 160 via a prism 180R and an image forming lens 200R which are described below.

Next, the structure of a rotating mechanism around the rotational axis $O_{22}$ is described.

A rotating shaft 190 is secured to the inclining block 161 and coaxial with the rotational axis $O_{22}$. The rotating shaft 190 is rotatable with respect to the right arm 158R of the U-shaped arm 158. A belt 191 is put around an end portion flange of the rotation shaft 190. On the other end side, the belt 191 is operatively coupled to a pulley 204 which is described below. Similarly, a rotating shaft 195 is secured to the inclining block 161 and coaxial with the rotational axis $O_{22}$. The rotating shaft 195 is rotatable around the rotational axis $O_{22}$ with respect to the right arm 158L of the U-shaped arm 158.

Next, the structure of a rotating mechanism around the rotational axis $O_{23}$ is described.

A rotating shaft 192 is secured to the image pick-up unit 162 and coaxial with the rotating axis $O_{23}$. The rotating shaft 192 is rotatable around the rotating axis $O_{23}$ with respect to the inclining block 161, and is provided in its upper end portion with a bevel gear 192a.

A connecting shaft 193 is inserted into the rotation shaft 190 and rotatable around the rotating axis $O_{22}$. The connecting shaft 193 is provided at its one end with a bevel gear 103a which meshes with the bevel gear 192a of the rotating shaft 192. A belt 194 is put around a flange at the other end of the connecting shaft 193. On the other end side, the belt 194 is operatively coupled to a pulley 206 which is described below. Similarly, a rotating shaft 196 is secured to the inclining block 161 coaxially with the rotaional axis $O_{23}$, and is rotatable around the rotational axis $O_{23}$ with respect to the image pick-up unit 162.

Figure 20:
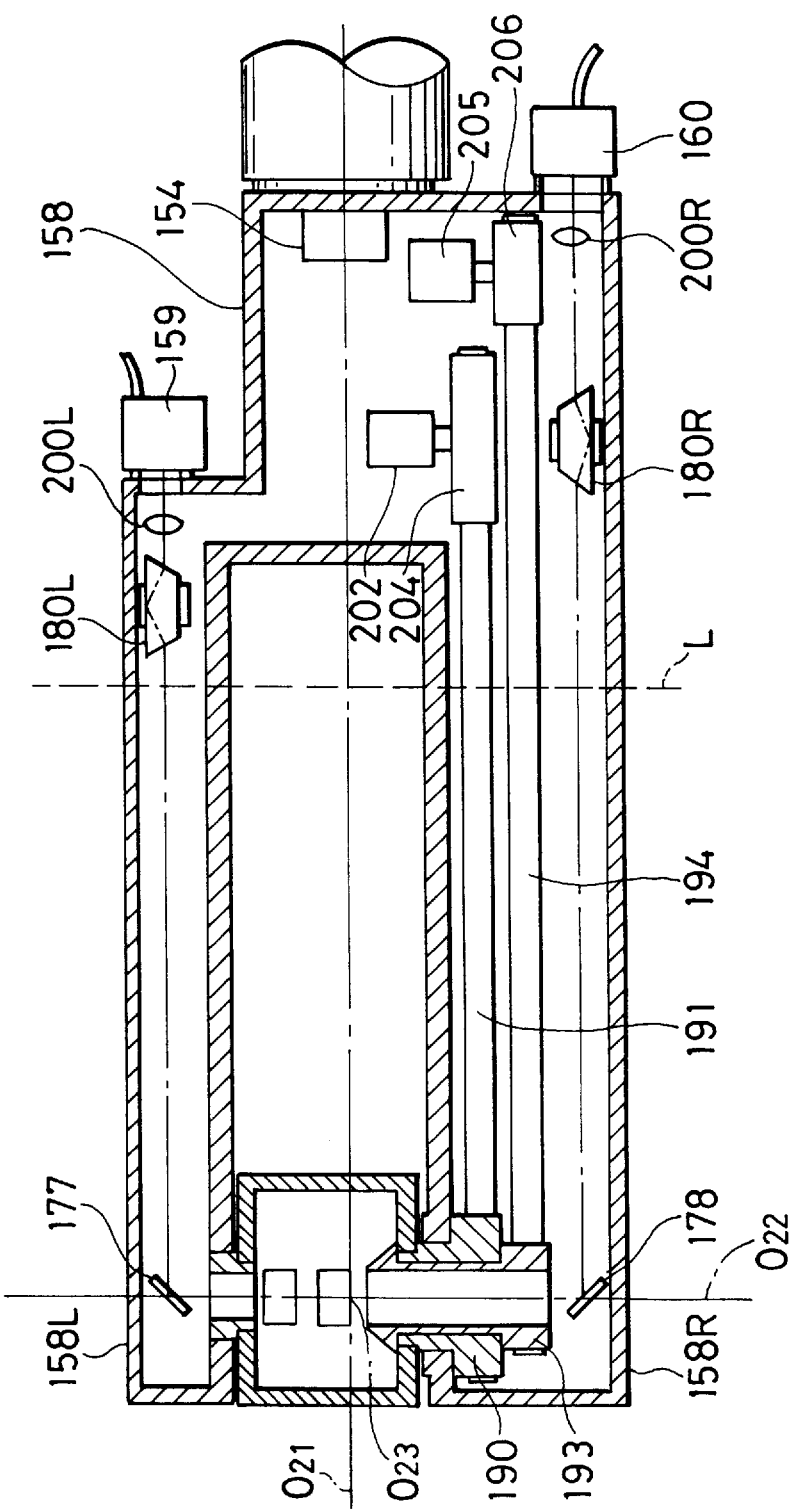
FIG. 20 is a cross-sectional view showing the U-shaped arm of FIG. 18 from above, taken in a plane containing rotational axes $O_{21}$ and $O_{22}$ of FIG. 18.

As shown in FIG. 20, the light reflected by the mirror 177 forms an image on a charge-coupled device (not shown) inside the television camera 159 via the image forming lens 200L secured to the U-shaped arm 158.

Similarly, the light reflected by the mirror 178 forms an image on a charge-coupled device (not shown) inside the television camera 160 via the image forming lens 200R secured to the U-shaped arm 158.

The prisms 180L and 180R are image rotating means provided in front of (that is, on the left side of) the lenses 200L and 200R, respectively. In order that an image rotated around the rotational axis $O_{23}$ between the inclining block 161 and the image pick-up unit 162 can be corrected, the prisms 180L and 180R can be rotated around the respective imaging optical axes 165 and 166 by motors (not shown).

The other end side of the belt 191 put around the rotating shaft 190 is put around the pulley 204 which is secured to a motor 202 provided to the U-shaped arm 158 and can be rotated around an axis parallel to the rotational axis $O_{22}$. Further, the other end side of the belt 194 put around the rotating shaft 193 is put around the pulley 206 which is secured to a motor 205 provided to the U-shaped arm 158 and can be rotated around an axis parallel to the rotational axis $O_{22}$.

In this embodiment, regarding rotation of the image pick-up unit 162 around the rotational axes $O_{22}$ and $O_{23}$, the belts 191 and 194 and the pulleys 204 and 206 constitute a power transmitting means. The rotating shaft 190 and the connecting shaft 193 composes a power output portion. The motors 202 and 205 construct a power generating portion.

Figure 21:
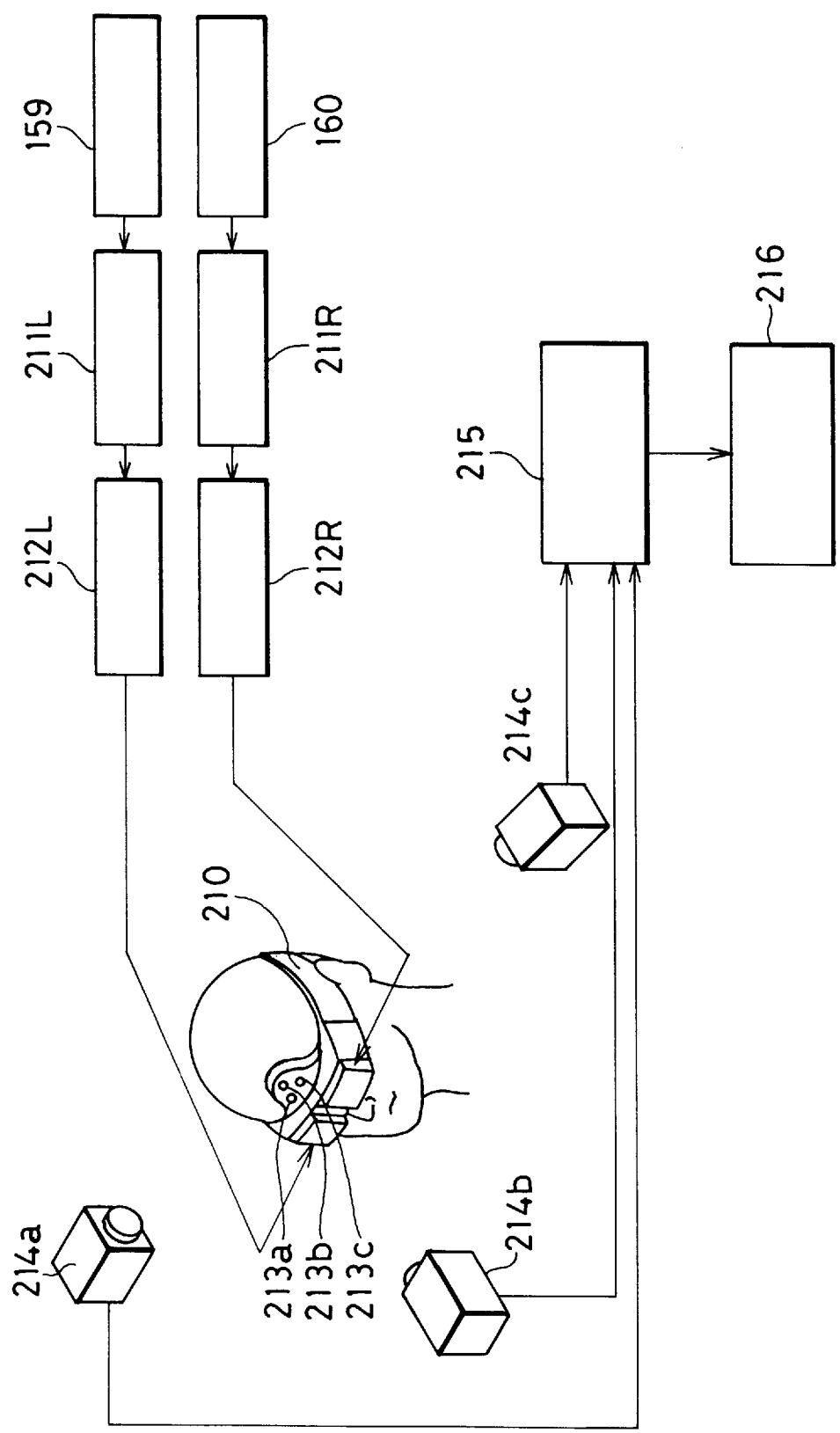
FIG. 21 is an illustration showing an operation instructing means of the operating microscope of the ninth embodiment.

FIG. 21 shows an operation instructing means of the apparatus. The operation instructing means is arranged in the control room (not shown) which is isolated from the MRI diagnosis apparatus.

A known head mount display (HMD) 210 attached to the head of a surgeon displays images picked up by the television cameras 159 and 160 in front of the left and right eyes of the surgeon via camera control units 211L and 211R and image processing units 212L and 212R. The head mount display 210 is provided with light-emitting diodes 213a, 213b, and 213c in a positional relationship shown in FIG. 21.

Image pick-up means 214a, 214b, and 214c for picking up the images of the light-emitting diodes 213a, 213b, and 213c are provided at positions in the control room which are prescribed by a program. Video signals of the image pick-up means 214a, 214b, and 214c are input into a computing means 215 which calculates the positions of the light-emitting diodes 213a, 213b, and 213c from the video signals, and the position and posture of the head mount display 210, namely the posture and observing direction of the surgeon, on the basis of the calculated values. According to the information from the computing means 215, a motor control means 216 outputs driving signals necessary for motors 152, 154, 155, 157, 202, and 205 in order to move and incline the image pick-up unit 162 to a position corresponding to the posture and observing direction of the surgeon.

Next, an operation of the ninth embodiment will be described.

In this embodiment, a surgical operation is performed by the surgeon in the control room which is isolated from the MRI diagnosis apparatus. The surgeon wears the head mount display 210 on his or her head and operates the operation manipulator while observing the image obtained by the image pick-up unit 162 of the operating microscope.

First, the shift of the observing position of the surgeon, namely the movement of the image pick-up unit 162, will be described. The image pick-up means 214a, 214b, and 214c pick up images of the light-emitting diodes 213a, 213b, and 213c of the head mount display 210 worn by the surgeon. According to the video signals output by the image pick-up means 214a, 214b, and 214c, the computing means 215 computes the positions (coordinates) of the light-emitting diodes 213a, 213b, and 213c. Even when the head of the surgeon, namely the light-emitting diodes 213a, 213b, and 213c move, new coordinates of the light-emitting diodes 213a, 213b, and 213c are calculated accordingly. Further, on the basis of the coordinates of the light-emitting diodes 213a, 213b, and 213c, the computing means 215 calculates the coordinates of a point being observed by the surgeon. According to the coordinate information of the posture and observing direction, the control means 216 calculates the rotation amounts of the motors 152, 154, 155, 157, 202, and 205 and the motors (not shown) for rotating the image rotating means 180L and 180R. The control means 216 then outputs the driving signals to rotate the respective motors.

Specifically, the movement and inclination of the image pick-up unit 162 in each direction will be described.

A vertical movement is accomplished by the extension and retraction of the support 151 due to the rotation of the motor 152. A horizontal movement is performed by a combination of the rotation of the block 153 around the vertical axis O20 due to the motor 154, and the extension and retraction of the arm 156 due to the motor 155.

An inclination around the rotational axis $O_{21}$ is effectuated by the rotation of the U-shaped arm 158 with respect to the arm 156 due to the rotation of the motor 157. An inclination around the rotational axis $O_{22}$ is accomplished in such a manner that the rotation of the pulley 204 secured to the motor 202 is translated into the rotation of the rotating shaft 190 around the rotational axis $O_{22}$ by the belt 191. A rotation around the rotational axis $O_{23}$ is performed in such a manner that the rotation of the pulley 206 secured to the motor 205 is translated into the rotation of the connecting shaft 193 around the rotational axis $O_{22}$ by the belt 191 and that the rotation of the connecting shaft 193 is translated into the rotation of the rotating shaft 192 since the bevel gear 193a meshes with the bevel gear 192a of the rotation shaft 192.

These operations enable the image pick-up unit 162 to move and incline at six degrees of freedom in response to the shift of the observing position of the surgeon.

Next, image transmission to the surgeon is described.

Light rays from the portion to be surgically operated go along the respective left and right imaging optical axes 165 and 166 via the objective lens 167, the magnification varying lenses 168L and 168R, the relay lenses 171 and 180, and the mirrors 172, 173, 174, 175, 177, 178, and 181 and the prism 176 provided on the respective optical axes. Then, the light rays enter the image rotating means 180L and 180R which adjust the directions of observed images in accordance with the rotation angle of the image pick-up unit 162 around the rotational axis $O_{23}$ so that they are kept constant. The observed images are formed in the television cameras 159 and 160 by the image forming lenses 200L and 200R.

Video signals from the television cameras 159 and 160 are input into the camera control units 211L and 211R and processed by the image processing units 212L and 212R, respectively, to display the images on left and right display portions of the head mount display 210.

Figure 10:
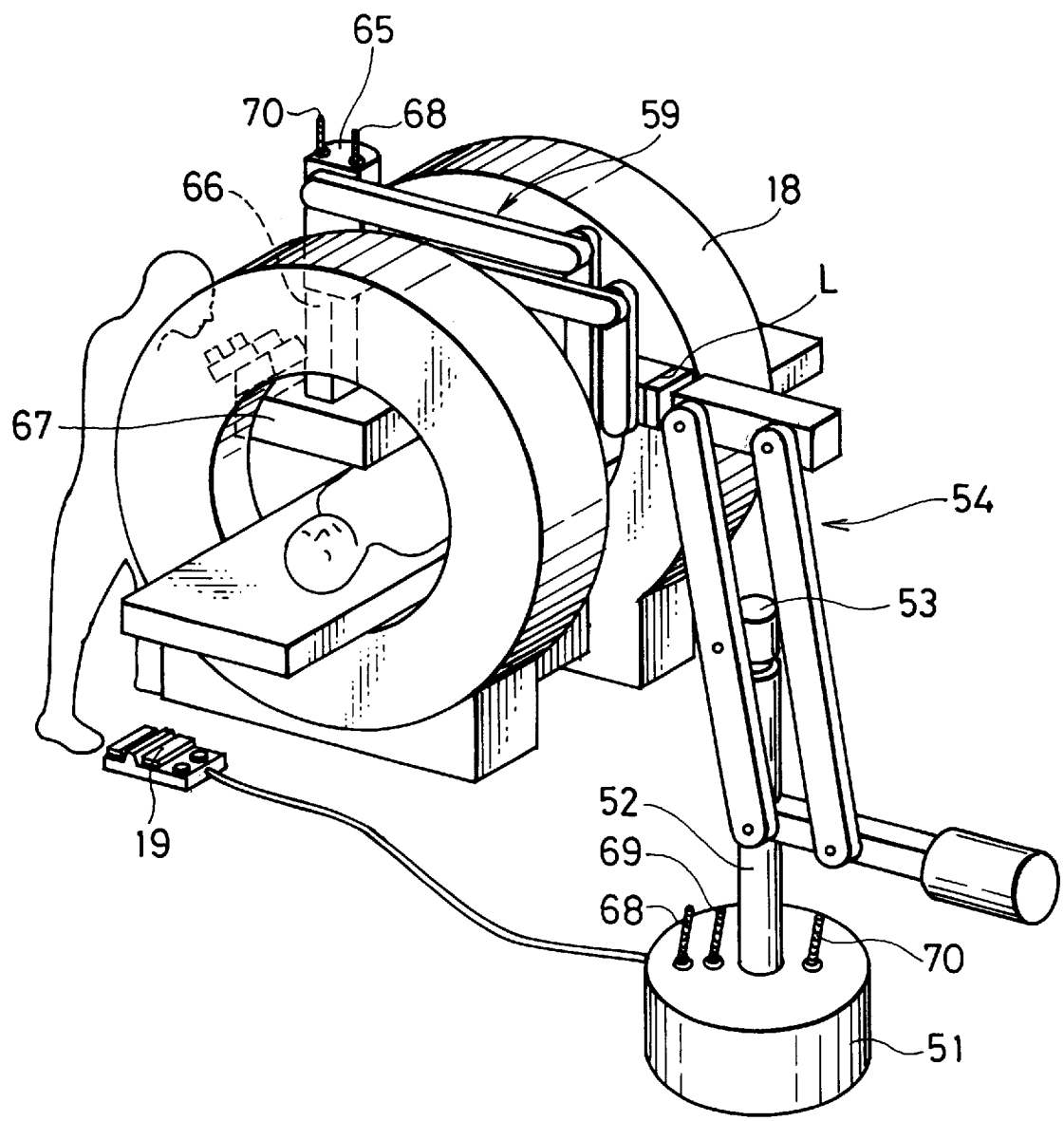
FIG. 10 is an outside view showing a combination of the operating microscope of the fifth embodiment and an MRI diagnosis apparatus.

Focusing and magnification varying of the image to be observed by the surgeon are performed by a foot switch as shown in FIGS. 3 or 10, or the like. Since the focusing and magnification varying operations are performed in the same way as in the fifth embodiment in which the slide shaft 80 is moved, their description is omitted.

In this embodiment, since the surgeon need not enter an intense magnetic field and a surrounding weak magnetic field of the MRI diagnosis apparatus, the surgeon need not take off a magnetic material from his or her body so that inconvenience will be reduced. Further, the surgeon will not be affected by the magnetic field.

Further, because a surgical operation can be performed remotely, disinfection and sterilization of the surgeon is not necessary and inconvenience will be reduced. In addition, one surgeon can perform a plurality of operations simultaneously.

Because the image of the portion to be surgically operated is transmitted from the image pick-up unit 162 by the optical elements, the television cameras 159 and 160 can be arranged where they will not be influenced by the magnetic field of the MRI diagnosis apparatus. Accordingly, conventional television cameras including magnetic materials may also be used.

A change of the observing position of the surgeon is detected by the combination of the head mount display 210, the light-emitting diodes 213a, 213b, and 213c, and the image pick-up means 214a, 214b, and 214c. On the basis of the results of the detection, the moving portions of the operating microscope are automatically moved. Therefore, the surgeon can perform a surgical operation as if he or she observes with the naked eye. Thus, there is no inconvenience of operating the operating microscope to shift the field of view so that the surgical operation can be performed efficiently.

Further, because the belts 191 and 194 are used for the transmission mechanisms for inclining the image pick-up unit 162, the structure is simple and it is quiet during a drive.

When the television cameras 159 and 160 are made of non-magnetic materials, they can be coupled directly to the image pick-up unit 162 which is in the intense magnetic field of the MRI diagnosis apparatus. In this case, are positioned on the respective imaging optical axes 165 and 166 behind the magnification varying lenses 168L and 168R of the image pick-up unit 162, and the television cameras 159 and 160 are arranged over the image forming lenses 200L and 200R. In this case, the optical elements and the image rotating means for transmitting the image to the television cameras are not necessary. Therefore, the operating microscope can be of a simple structure and a light weight.

As a further variation, an eyepiece lens of a conventional operating microscope may be positioned where the magnetic field of the MRI diagnosis apparatus does not influence the eyepiece lens, and in order to transmit the image of the portion to be surgically operated to the eyepiece lens, the mirrors and prisms described in this embodiment, and other known optical elements, such as glass fibers, may be arbitrarily combined. Accordingly, the surgeon can perform a surgical operation in the same way as a conventional operation by observing the optical image with the naked eye. Moreover, a system for transmitting and displaying the video image will not be necessary so that the structure can be simple.

In this embodiment, the surgeon observes the three-dimensional image by using the head mount display 210. However, a known three-dimensional monitor and a known three-dimensional converter may be used as a means for displaying the three-dimensional image so that the surgeon can observe the image on the monitor.

The power transmitting means of this embodiment comprises the pulleys, the belts, and the bevel gears. However, the pulleys and the belts can be replaced with link mechanisms. With this structure, operation response will be enhanced because the component members for the transmission are rigid. Further, the pulleys and the belts of the power transmitting means can be replaced with a known transmission means, such as gears.

The input portion for changing the observing position, namely for moving and inclining the image pick-up unit 162 may be composed of a combination of a joystick, a three-dimensional mouse and the like. In this case, the system is simple and inexpensive.

In this embodiment, the optical system for image transmission has components on the left and right sides. However, even if the optical system has components on only one side, its function and effect will not change.

Figure 22:
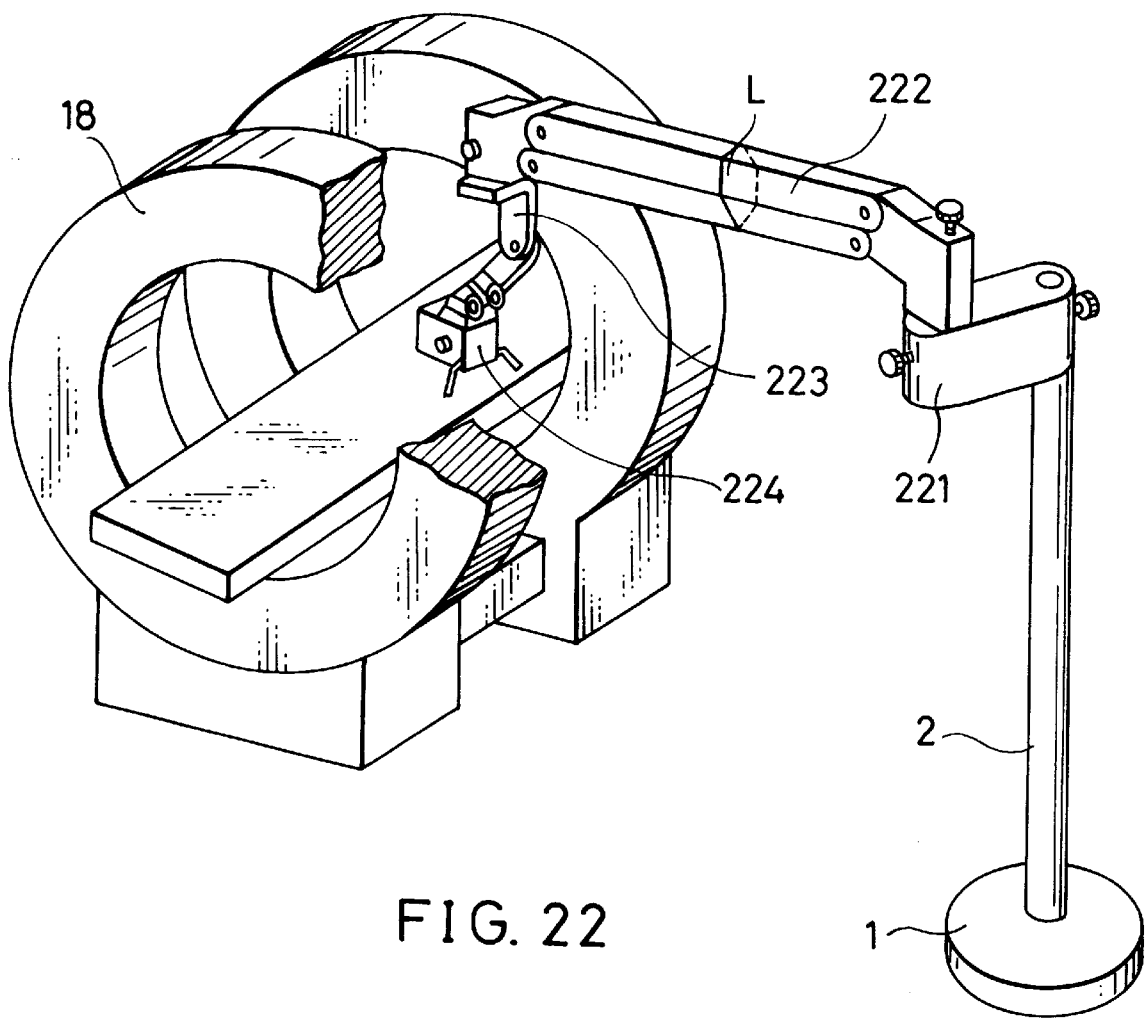
FIG. 22 is an external view showing a combination of an operating microscope for manual operation of a tenth embodiment of this invention and an MRI diagnosis apparatus.

Referring to FIG. 22, an operating microscope according to a tenth embodiment of this invention will be described.

The operating microscope of this embodiment is a manual operating microscope which is basically the same as the operating microscope of the first embodiment except that the power generating portion, the power transmitting means, and the power output portion of the first embodiment are excluded. Thus, the same parts as those of the first embodiment will not be described.

A base 1 is movable in an operating room and a support 2 is vertically secured to the base 1. A first arm 221 is supported by the support 2 so as to rotate and move up and down. A second arm 222 comprises a parallelogram link which is supported by a distal end portion of the first arm 221 so as to rotate around a vertical axis. A distal end portion of the second arm 222 can move up and down owing to the parallelogram link and holds a microscope portion 224 via a microscope portion mounting arm 223.

The microscope portion mounting arm 223 can move and direct the microscope portion 224 to an arbitrary observed position and hold the microscope portion 224 in that position.

Non-magnetic materials are used for the distal end portion side of the second arm 222 beyond a border plane L, the microscope portion mounting arm 223, and the microscope portion 224.

In operation, a surgeon moves the base 1, namely the whole operating microscope, and positions the operating microscope so that its distal end portion side beyond the border plane L is used inside the MRI diagnosis apparatus. The microscope portion 224 is moved in such a manner that the first arm 221 is manually moved up and down with respect to the support 2, that the first arm 221 is rotated with respect to the support 2, that the second arm 222 is rotated with respect to the first arm 221, that the microscope portion mounting arm 223 is rotated with respect to the second arm 222, and that the parallelogram link of the second arm 222 is moved up and down.

Because the operating microscope of this embodiment has no driving portion made of a magnetic material, such as a motor, it is not necessary to take into consideration where to position the motor, a power transmitting means, and the like. Therefore, the operating microscope can be compact, lightweight, and inexpensive.

Figure 23:
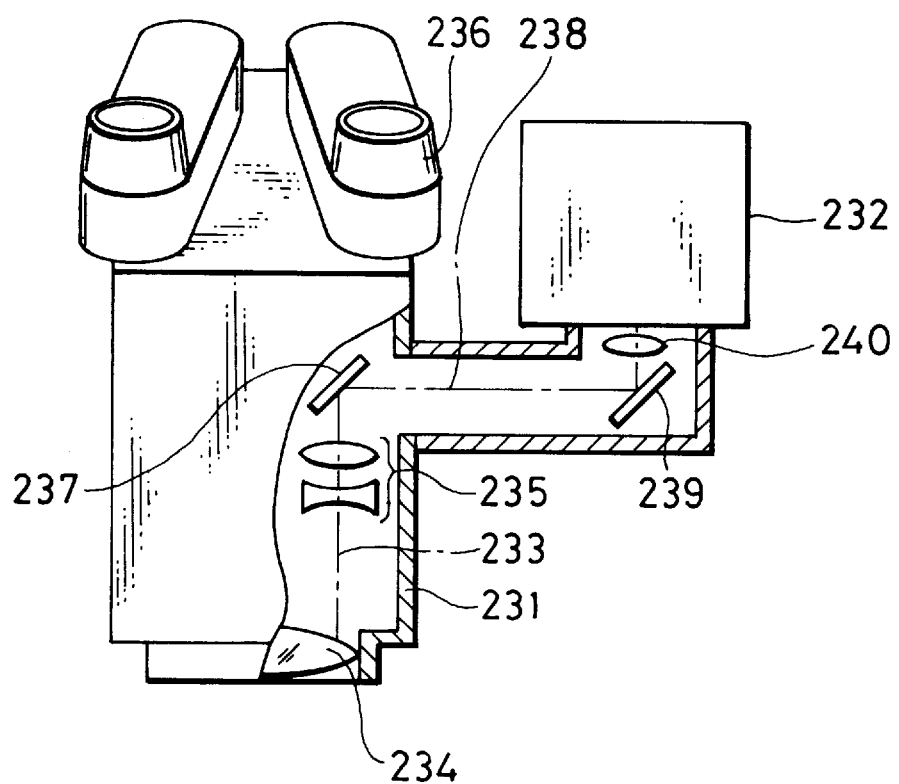
FIG. 23 is an illustration showing a connection of a microscope portion of an operating microscope of an eleventh embodiment of this invention and a television camera.

Referring to FIG. 23, an operating microscope according to an eleventh embodiment of this invention will be described.

The microscope portion 6 of the first, second, and third embodiments, the microscope portion 42 of the fourth embodiment, the microscope portion 67 of the fifth embodiment, and the microscope portion 224 of the tenth embodiment have eyepiece portions only. However, as shown in FIG. 23, in the eleventh embodiment, a microscope portion 231 is provided with a television camera 232 functioning as an image pick-up means. Description of the same parts as those of other embodiments is omitted.

Referring to FIG. 23, an imaging optical system will be described.

In the order from the object side on a left or right observing optical axis 233, an objective lens 234 and a magnification varying lens 235 are provided. The objective lens 234 is fixed to the microscope portion 231. The magnification varying lens 235 is supported by the microscope portion 231 so as to be advanceable and retractable along the observation optical axis 233. A transmission mechanism for advancing and retracting the magnification varying lens 235 has the same structure as that shown in FIGS. 8 and 9 for driving the slide shaft 80 of the fifth embodiment. Therefore, its description is omitted.

On the observing optical axis 233 above the magnification varying lenses 235, a half mirror 237 is fixed to the microscope portion 231. The half mirror 237 divides a light beam passing through the magnification varying lens 235 into two parts which are led to an eyepiece portion 236 and a television camera 232, respectively. The light beam passing through the half mirror 237 forms an image at the eyepiece portion 236 observable by a surgeon.

The light beam reflected by the half mirror 237 goes along an imaging optical axis 238, is reflected by a total reflection mirror 239 fixed to the microscope portion 231, and reaches the television camera 232 via an image forming lens 240.

An image picked up by the television camera 232 is displayed on a monitor (not shown) functioning as a display means, via a signal cable (not shown) functioning as an image transmitting means.

Non-magnetic materials are used for all of the microscope portion 231, the eyepiece portion 236, and the television camera 232 shown in FIG. 23, and the signal cable, a power output portion, and a power transmitting portion which are not shown.

This embodiment does not require an optical element for transmitting an image to the television camera, an image rotation means, and the like. Therefore, the operating microscope can be of a simple structure and a light weight.

Because the image is observed on the monitor, the surgeon need not enter an intense magnetic field and a surrounding weak magnetic field of an MRI diagnosis apparatus. Therefore, the surgeon need not take off a magnetic material from his or her body so that inconvenience will be reduced. Further, the surgeon will not be influenced by the magnetic field.

What is claimed is:

1. An operating microscope comprising:

a base;

a support coupled to the base;

an arm having a proximal end portion rotatably and vertically movably coupled to the support, and a distal end portion, at least the distal end portion being formed of a non-magnetic material;

a microscope portion coupled to the distal end portion of the arm and including a stereoscopic optical system for forming an image of an observed part, the microscope portion being formed of a non-magnetic material;

power means for operating the microscope portion or a part thereof; and operation instructing means for instructing the power means to operate;

the power means comprising:

a power generating portion for generating a power for operating;

a power output portion, formed of a non-magnetic material, for operating the microscope portion or a part thereby by the power generated by the power generating portion; and power transmitting means for transmitting the power for operating from the power generating portion to the power output portion, the power transmitting means being formed of a non-magnetic material in the microscope portion and the non-magnetic portion of the arm.

2. The operating microscope according to claim 1, further comprising microscope portion changing and fixing means connected between the distal end portion of the arm and the microscope portion for arbitrarily changing and fixing a position or a direction of the microscope portion, the microscope portion changing and fixing means being formed of a non-magnetic material.

3. The operating microscope according to claim 1, further comprising observed position detecting means for detecting a position being observed by a surgeon and for outputting a signal, wherein in response to the signal from the observed position detecting means, at least one of the power means and microscope portion changing and fixing means is operated such that the microscope portion is directed towards a position which the surgeon intends to observe.

4. The operating microscope according to claim 1, further comprising:

optical image transmitting means for optically transmitting the image of the observed part formed by the stereoscopic optical system, the optical image transmitting means being formed of a non-magnetic material at least in a distal end portion thereof; and an observing portion for observing the image of the observed part transmitted by the optical image transmitting means.

5. The operating microscope according to claim 4, further comprising:

image pick-up means for picking up the image transmitted from the optical image transmitting means; and image transmitting means for transmitting the image of the observed part picked up by the image pick-up means.

6. The operating microscope according to claim 1, wherein the arm is provided with the power generating portion, wherein the power output portion is arranged in one of the microscope portion and the non-magnetic portion of the arm connected to the microscope portion, and wherein the power transmitting means can follow a change of a relative position of the power generating portion with respect to the power output portion.

7. The operating microscope according to claim 1, wherein the base is provided with the power generating portion, wherein the power output portion is arranged in one of the microscope portion and the non-magnetic portion of the arm connected to the microscope portion, and wherein the power transmitting means can follow a change of a relative position of the power generating portion with respect to the power output portion.

8. The operating microscope according to claim 1, wherein the power transmitting means is a link mechanism.

9. The operating microscope according to claim 1, wherein the power transmitting portion is a wire transmitting system comprising a non-magnetic inner and a non-magnetic outer.

10. The operating microscope according to claim 1, wherein the power transmitting means is a hydraulic transmitting mechanism comprising a non-magnetic oil and a non-magnetic oil tube.

11. The operating microscope according to claim 1, wherein the power generating portion comprises an air compressor, wherein the power transmitting means comprises a non-magnetic air tube for keeping air pressure constant at an end of the power generating portion and an end of the power output means, and wherein the power output means comprises a non-magnetic air cylinder.

12. The operating microscope according to claim 1, wherein the power generating portion comprises an air pump, wherein the power transmitting means comprises a non-magnetic air tube for transmitting air, and wherein the power output means comprises a non-magnetic air turbine.

13. An operating microscope comprising:

a base;

a support coupled to the base;

an arm having a proximal end portion rotatably and vertically movably coupled to the support, and a distal end portion, at least the distal end portion being formed of a non-magnetic material;

a microscope portion coupled to the distal end portion of the arm and including a stereoscopic optical system for forming an image of an observed part, the microscope portion being formed of a non-magnetic material;

power means for operating the microscope portion or a part thereof; and operation instructing means for instructing the power means to operate;

the power means comprising:

a power generating portion for generating a power for driving;

power output portion, formed of a non-magnetic material, for driving the microscope portion or a part thereof by the power generated by the power generating portion;

power transmitting means for transmitting the power for driving from the power generating portion to the power output portion, the power transmitting means being formed of a non-magnetic material in the microscope portion and the non-magnetic portion of the arm; and observed position detecting means for detecting a position being observed by a surgeon and for outputting a signal, wherein in response to the signal from the observed position detecting means, at least one of the power means and microscope portion changing and fixing means is operated such that the microscope portion is directed towards a position which the surgeon intends to observe.

14. An operating microscope system comprising an operating microscope and an MRI diagnosis apparatus, the operating microscope comprising:

a support;

an arm rotatably and vertically movably coupled to the support, at least a distal end portion of the arm being formed of a non-magnetic material; and a microscope portion fixed to the distal end portion of the arm and including a stereoscopic optical system for forming an image of an observed part, the microscope portion being formed of a non-magnetic material, wherein at least a part of the non-magnetic portions of the operating microscope is arranged in the MRI diagnosis apparatus.

15. The operating microscope system according to claim 14, further comprising microscope portion changing and fixing means connected between the distal end portion of the arm and the microscope portion for arbitrarily changing and fixing a position or a direction of the microscope portion, the microscope portion changing and fixing means being formed of a non-magnetic material.

16. The operating microscope system according to claim 14, further comprising:

power means for operating the microscope portion or a part thereof; and operation instructing means for instructing the power means to operate;

the power means comprising:

a power generating portion for generating a power for operating;

power output portion, formed of a non-magnetic material, for operating the microscope portion or a part thereof by the power generated by the power generating portion; and power transmitting means for transmitting the power for operating from the power generating portion to the power output portion, the power transmitting means being formed of a non-magnetic material in the microscope portion and the non-magnetic portion of the arm, wherein at least a part of the non-magnetic portions of the power means is arranged in the MRI diagnosis apparatus.

17. The operating microscope system according to claim 16, wherein the arm is provided with the power generating portion, wherein the power output portion is arranged in one of the microscope portion and the non-magnetic portion of the arm connected to the microscope portion, and wherein the power transmitting means can follow a change of a relative position of the power generating portion with respect to the power output portion.

18. The operating microscope system according to claim 17, wherein the power generating portion is arranged in the arm and outside of the MRI diagnosis apparatus.

19. The operating microscope system according to claim 16, further comprising observed position detecting means for detecting a position being observed by a surgeon and for outputting a signal, wherein in response to the signal from the observed position detecting means, at least one of the power means and microscope portion changing and fixing means is operated such that the microscope portion is directed towards a position which the surgeon intends to observe.

20. The operating microscope according to claim 16, wherein the base is provided with the power generating portion, wherein the power output portion is arranged in one of the microscope portion and the non-magnetic portion of the arm connected to the microscope portion, and wherein the power transmitting means can follow a change of a relative position of the power generating portion with respect to the power output portion.

21. The operating microscope according to claim 16, wherein the power transmitting means is a link mechanism.

22. The operating microscope according to claim 16, wherein the power transmitting portion is a wire transmitting system comprising a non-magnetic inner and a non-magnetic outer.

23. The operating microscope according to claim 16, wherein the power transmitting means is a hydraulic transmitting mechanism comprising a non-magnetic oil and a non-magnetic oil tube.

24. The operating microscope according to claim 16, wherein the power generating portion comprises an air compressor, wherein the power transmitting means comprises a non-magnetic air tube for keeping air pressure constant at an end of the power generating portion and an end of the power output means, and wherein the power output means comprises a non-magnetic air cylinder.

25. The operating microscope according to claim 16, wherein the power generating portion comprises an air pump, wherein the power transmitting means comprises a non-magnetic air tube for transmitting air, and wherein the power output means comprises a non-magnetic air turbine.

26. The operating microscope system according to claim 14, further comprising:

image pick-up means for picking up the image of the observed part formed by the stereoscopic optical system, the image pick-up means being formed on a non-magnetic material;

image transmitting means for transmitting the image of the observed part picked up by the image pick-up means, the image transmitting means being formed of a non-magnetic material at least on a microscope portion side thereof; and display means for displaying the image of the observed part transmitted by the image transmitting means, wherein at least a part of the non-magnetic portions of the image pick-up means and the image transmitting means are arranged in the MRI diagnosis apparatus.

27. The operating microscope system according to claim 14, further comprising;

optical image transmitting means for optically transmitting the image of the observed part formed by the stereoscopic optical system, the optical image transmitting means being formed of a non-magnetic material at least in a distal end portion thereof; and an observing portion for observing the image of the observed part transmitted by the optical image transmitting means, wherein at least a part of the non-magnetic portion of the optical image transmitting means is arranged in the MRI diagnosis apparatus.

28. The operating microscope according to claim 27, further comprising:

image pick-up means for picking up the image transmitted from the optical image transmitting means; and image transmitting means for transmitting the image of the observed part picked up by the image pick-up means.

* * * * *